United States Patent
Chatterjee et al.

(10) Patent No.: US 12,385,024 B2
(45) Date of Patent: Aug. 12, 2025

(54) APPLICATIONS OF ENGINEERED STREPTOCOCCUS CANIS Cas9 VARIANTS ON SINGLE-BASE PAM TARGETS

(71) Applicant: Massachusetts Institute of Technology, Cambridge, MA (US)

(72) Inventors: Pranam Chatterjee, Durham, NC (US); Noah Michael Jakimo, Boston, MA (US); Joseph M. Jacobson, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/220,808

(22) Filed: Jul. 11, 2023

(65) Prior Publication Data
US 2024/0141309 A1 May 2, 2024

Related U.S. Application Data

(60) Division of application No. 17/855,507, filed on Jun. 30, 2022, now Pat. No. 11,697,808, which is a division of application No. 16/689,071, filed on Nov. 19, 2019, now Pat. No. 11,453,865, which is a continuation-in-part of application No. 16/136,238, filed on Sep. 19, 2018, now abandoned.

(60) Provisional application No. 62/769,520, filed on Nov. 19, 2018, provisional application No. 62/560,630, filed on Sep. 19, 2017.

(51) Int. Cl.
| | |
|---|---|
| *C12N 9/22* | (2006.01) |
| *C12N 15/11* | (2006.01) |
| *C12N 15/85* | (2006.01) |

(52) U.S. Cl.
CPC ........... *C12N 9/22* (2013.01); *C12N 15/11* (2013.01); *C12N 15/85* (2013.01); *C12N 2310/20* (2017.05); *C12N 2800/80* (2013.01)

(58) Field of Classification Search
CPC ....................................................... C12N 9/22
See application file for complete search history.

(56) References Cited

PUBLICATIONS

Chaterjee et al., "Minimal PAM specificity of a highly similar SpCas9 ortholog", Science Advances, 2018, 4: eaau0766. pp. 1-10.*
Anders et al., "Structural basis of PAM-dependent target DNA recognition by the Cas9 endonuclease", Nature, 2014, 513(7519), pp. 569-573.*
Nishimasu et al., "Engineered CRISPR-Cas9 nuclease with expanded targeting space" Science, Sep. 21, 2018;361(6408):1259-1262. doi: 10.1126/science.aas9129. Epub Aug. 30, 2018.*

* cited by examiner

*Primary Examiner* — Suzanne M Noakes
(74) *Attorney, Agent, or Firm* — Norma E. Henderson

(57) ABSTRACT

Engineered *Streptococcus canis* Cas9 (ScCas9) variants include an ScCas9 protein with its PID being the PID amino acid composition of *Streptococcus pyogenes* Cas9 (SpCas9-NG, an ScCas9 protein having a threonine-to-lysine substitution mutation at position 1227 in its amino acid sequence (Sc+), and an ScCas9 protein having a threonine-to-lysine substitution mutation at position 1227 and a substitution of residues ADKKLRKRSGKLATE [SEQ ID No. 4] in position 365-379 in the ScCas9 open reading frame (Sc++). Also included are CRISPR-associated DNA endonucleases with a PAM specificity of 5'-NG-3' or 5'-NNG-3' and a method of altering expression of a gene product by utilizing the engineered ScCas9 variants.

8 Claims, 23 Drawing Sheets
Specification includes a Sequence Listing.

Fig. 1

| | Label | Events | Percent gated |
|---|---|---|---|
| Sp | all | 14923 | 100.00 |
| | GFP+ | 778 | 5.21 |

| | Label | Events | Percent gated |
|---|---|---|---|
| ScSp | all | 14822 | 100.00 |
| | GFP+ | 932 | 6.29 |

| | Label | Events | Percent gated |
|---|---|---|---|
| Sc | all | 14927 | 100.00 |
| | GFP+ | 1071 | 7.17 |

| | Label | Events | Percent gated |
|---|---|---|---|
| SpNG | all | 14821 | 100.00 |
| | GFP+ | 1007 | 6.79 |

| | Label | Events | Percent gated |
|---|---|---|---|
| ScNG | all | 14822 | 100.00 |
| | GFP+ | 1068 | 7.21 |

| | Label | Events | Percent gated |
|---|---|---|---|
| Sc+ | all | 14969 | 100.00 |
| | GFP+ | 1517 | 10.13 |

8N Library

```
                           SEQUENCE LISTING

Sequence total quantity: 43
SEQ ID NO: 1              moltype = DNA  length = 20
FEATURE                   Location/Qualifiers
source                    1..20
                          mol_type = genomic DNA
                          organism = Streptococcus canis
SEQUENCE: 1
ccgctgacaa cattgttggc                                                    20

SEQ ID NO: 2              moltype = DNA  length = 20
FEATURE                   Location/Qualifiers
source                    1..20
                          mol_type = genomic DNA
                          organism = Streptococcus canis
SEQUENCE: 2
tttcaatggt aagatcattc                                                    20

SEQ ID NO: 3              moltype = DNA  length = 20
FEATURE                   Location/Qualifiers
source                    1..20
                          mol_type = genomic DNA
                          organism = Streptococcus canis
SEQUENCE: 3
gtttacgctc atcagataga                                                    20

SEQ ID NO: 4              moltype = AA   length = 15
FEATURE                   Location/Qualifiers
REGION                    1..15
                          note = substitute residues in position 365-379 in the
                           ScCas9 open reading frame
source                    1..15
                          mol_type = protein
                          organism = synthetic construct
SEQUENCE: 4
ADKKLRKRSG KLATE                                                         15

SEQ ID NO: 5              moltype = DNA  length = 20
FEATURE                   Location/Qualifiers
source                    1..20
                          mol_type = genomic DNA
                          organism = Streptococcus canis
SEQUENCE: 5
cgaaaggttt tgcactcgac                                                    20

SEQ ID NO: 6              moltype = DNA  length = 20
FEATURE                   Location/Qualifiers
source                    1..20
                          mol_type = genomic DNA
                          organism = Streptococcus canis
SEQUENCE: 6
ttctgtagtc gacggtaccg                                                    20

SEQ ID NO: 7              moltype = DNA  length = 20
FEATURE                   Location/Qualifiers
source                    1..20
                          mol_type = genomic DNA
                          organism = Streptococcus canis
SEQUENCE: 7
ggagggtggc gagaggggcc                                                    20

SEQ ID NO: 8              moltype = DNA  length = 20
FEATURE                   Location/Qualifiers
source                    1..20
                          mol_type = genomic DNA
                          organism = Streptococcus canis
SEQUENCE: 8
tctgacaata gtcctgtctg                                                    20
```

```
SEQ ID NO: 9                moltype = DNA   length = 20
FEATURE                     Location/Qualifiers
source                      1..20
                            mol_type = genomic DNA
                            organism = Streptococcus canis
SEQUENCE: 9
aaatgaatga atgagcagat                                                       20

SEQ ID NO: 10               moltype = DNA   length = 20
FEATURE                     Location/Qualifiers
source                      1..20
                            mol_type = genomic DNA
                            organism = Streptococcus canis
SEQUENCE: 10
ccagaagaat ggtgtcatta                                                       20

SEQ ID NO: 11               moltype = DNA   length = 20
FEATURE                     Location/Qualifiers
source                      1..20
                            mol_type = genomic DNA
                            organism = Streptococcus canis
SEQUENCE: 11
atttcattac aggcaaagct                                                       20

SEQ ID NO: 12               moltype = DNA   length = 20
FEATURE                     Location/Qualifiers
source                      1..20
                            mol_type = genomic DNA
                            organism = Streptococcus canis
SEQUENCE: 12
gaaaatgcac cctcttctga                                                       20

SEQ ID NO: 13               moltype = DNA   length = 20
FEATURE                     Location/Qualifiers
source                      1..20
                            mol_type = genomic DNA
                            organism = Streptococcus canis
SEQUENCE: 13
gctgaaacag tgacctgtct                                                       20

SEQ ID NO: 14               moltype = DNA   length = 20
FEATURE                     Location/Qualifiers
source                      1..20
                            mol_type = genomic DNA
                            organism = Streptococcus canis
SEQUENCE: 14
aaacaccatg taccacacat                                                       20

SEQ ID NO: 15               moltype = DNA   length = 20
FEATURE                     Location/Qualifiers
source                      1..20
                            mol_type = genomic DNA
                            organism = Streptococcus canis
SEQUENCE: 15
ggattcctgg tgccagaaac                                                       20

SEQ ID NO: 16               moltype = DNA   length = 20
FEATURE                     Location/Qualifiers
source                      1..20
                            mol_type = genomic DNA
                            organism = Streptococcus canis
SEQUENCE: 16
gttaacagct gacccaataa                                                       20

SEQ ID NO: 17               moltype = DNA   length = 20
FEATURE                     Location/Qualifiers
source                      1..20
                            mol_type = genomic DNA
                            organism = Streptococcus canis
SEQUENCE: 17
atgtgaacgg acagattgac                                                       20

SEQ ID NO: 18               moltype = DNA   length = 20
FEATURE                     Location/Qualifiers
source                      1..20
                            mol_type = genomic DNA
                            organism = Streptococcus canis
SEQUENCE: 18
```

```
ggtctagaac cctctgggga                                                   20

SEQ ID NO: 19          moltype = DNA   length = 20
FEATURE                Location/Qualifiers
source                 1..20
                       mol_type = genomic DNA
                       organism = Streptococcus canis
SEQUENCE: 19
gcaccagcgg acccacacgg                                                   20

SEQ ID NO: 20          moltype = DNA   length = 20
FEATURE                Location/Qualifiers
source                 1..20
                       mol_type = genomic DNA
                       organism = Streptococcus canis
SEQUENCE: 20
cattctggtc atgcaccaga                                                   20

SEQ ID NO: 21          moltype = DNA   length = 20
FEATURE                Location/Qualifiers
source                 1..20
                       mol_type = genomic DNA
                       organism = Streptococcus canis
SEQUENCE: 21
acagggaga aaccctacga                                                    20

SEQ ID NO: 22          moltype = DNA   length = 20
FEATURE                Location/Qualifiers
source                 1..20
                       mol_type = genomic DNA
                       organism = Streptococcus canis
SEQUENCE: 22
gatgtgtgat aaagttagag                                                   20

SEQ ID NO: 23          moltype = DNA   length = 20
FEATURE                Location/Qualifiers
source                 1..20
                       mol_type = genomic DNA
                       organism = Streptococcus canis
SEQUENCE: 23
gccagtctcg atccgccccg                                                   20

SEQ ID NO: 24          moltype = DNA   length = 20
FEATURE                Location/Qualifiers
source                 1..20
                       mol_type = genomic DNA
                       organism = Streptococcus canis
SEQUENCE: 24
gcggatcgag actggcaacg                                                   20

SEQ ID NO: 25          moltype = DNA   length = 20
FEATURE                Location/Qualifiers
source                 1..20
                       mol_type = genomic DNA
                       organism = Streptococcus canis
SEQUENCE: 25
gctcggccac cacagggaag                                                   20

SEQ ID NO: 26          moltype = AA    length = 1368
FEATURE                Location/Qualifiers
source                 1..1368
                       mol_type = protein
                       organism = Streptococcus pyogenes
SEQUENCE: 26
MDKKYSIGLD IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
```

```
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 27          moltype = AA   length = 1375
FEATURE                Location/Qualifiers
source                 1..1375
                       mol_type = protein
                       organism = Streptococcus canis
SEQUENCE: 27
MEKKYSIGLD IGTNSVGWAV ITDDYKVPSK KFKVLGNTNR KSIKKNLMGA LLFDSGETAE    60
ATRLKRTARR RYTRRKNRIR YLQEIFANEM AKLDDSFFQR LEESFLVEED KKNERHPIFG   120
NLADEVAYHR NYPTIYHLRK KLADSPEKAD LRLIYLALAH IIKFRGHFLI EGKLNAENSD   180
VAKLFYQLIQ TYNQLFEESP LDEIEVDAKG ILSARLSKSK RLEKLIAVFP NEKKNGLFGN   240
IIALALGLTP NFKSNFDLTE DAKLQLSKDT YDDDLDELLG QIGDQYADLF SAAKNLSDAI   300
LLSDILRSNS EVTKAPLSAS MVKRYDEHHQ DLALLKTLVR QQFPEKYAEI FKDDTKNGYA   360
GYVGIGIKHR KRTTKLATQE EFYKFIKPIL EKMDGAEELL AKLNRDDLLR KQRTFDNGSI   420
PHQIHLKELH AILRRQEEFY PFLKENREKI EKILTFRIPY YVGPLARGNS RFAWLTRKSE   480
EAITPWNFEE VVDKGASAQS FIERMTNFDE QLPNKKVLPK HSLLYEYFTV YNELTKVKYV   540
TERMRKPEFL SGEQKKAIVD LLFKTNRKVT VKQLKEDYFK KIECFDSVEI IGVEDRFNAS   600
LGTYHDLLKI IKDKDFLDNE ENEDILEDIV LTLTLFEDRE MIEERLKTYA HLFDDKVMKQ   660
LKRRHYTGWG RLSRKMINGI RDKQSGKTIL DFLKSDGFSN RNFMQLIHDD SLTFKEEIEK   720
AQVSGQGDSL HEQIADLAGS PAIKKGILQT VKIVDELVKV MGHKPENIVI EMARENQTTT   780
KGLQQSRERK KRIEEGIKEL ESQILKENPV ENTQLQNEKL YLYYLQNGRD MYVDQELDIN   840
RLSDYDVDHI VPQSFIKDDS IDNKVLTRSV ENRGKSDNVP SEEVVKKMKN YWRQLLNAKL   900
ITQRKFDNLT KAERGGLSEA DKAGFIKRQL VETRQITKHV ARILDSRMNT KRDKNDKPIR   960
EVKVITLKSK LVSDFRKDFQ LYKVRDINNY HHAHDAYLNA VVGTALIKKY PKLESEFVYG  1020
DYKVYDVRKM IAKSEQEIGK ATAKRFFYSN IMNFFKTEVK LANGEIRKRP LIETNGETGE  1080
VVWNKEKDFA TVRKVLAMPQ VNIVKKTEVQ TGGFSKESIL SKRESAKLIP RKKGWDTRKY  1140
GGFGSPTVAY SILVVAKVEK GKAKKLKSVK VLVGITIMEK GSYEKDPIGF LEAKGYKDIK  1200
KELIFKLPKY SLFELENGRR RMLASATELQ KANELVLPQH LVRLLYYTQN ISATTGSNNL  1260
GYIEQHREEF KEIFEKIIDF SEKYILKNKV NSNLKSSFDE QFAVSDSILL SNSFVSLLKY  1320
TSFGASGGFT FLDLDVKQGR LRYQTVTEVL DATLIYQSIT GLYETRTDLS QLGGD       1375

SEQ ID NO: 28          moltype = DNA   length = 23
FEATURE                Location/Qualifiers
source                 1..23
                       mol_type = genomic DNA
                       organism = Homo sapiens
SEQUENCE: 28
ggtgagtgag tgtgtgcgtg tgg                                            23

SEQ ID NO: 29          moltype = DNA   length = 23
FEATURE                Location/Qualifiers
source                 1..23
                       mol_type = genomic DNA
                       organism = Homo sapiens
SEQUENCE: 29
gctgcagaag ggattccatg agg                                            23

SEQ ID NO: 30          moltype = DNA   length = 23
FEATURE                Location/Qualifiers
source                 1..23
                       mol_type = genomic DNA
                       organism = Homo sapiens
SEQUENCE: 30
ggagtgaggg aaacggcccc agg                                            23

SEQ ID NO: 31          moltype = DNA   length = 23
FEATURE                Location/Qualifiers
source                 1..23
                       mol_type = genomic DNA
                       organism = Homo sapiens
SEQUENCE: 31
agtgagtgag tgtgtgtgtg ggg                                            23

SEQ ID NO: 32          moltype = DNA   length = 23
FEATURE                Location/Qualifiers
source                 1..23
                       mol_type = genomic DNA
                       organism = Homo sapiens
SEQUENCE: 32
gctgcagaag ggattccaag ggg                                            23
```

```
SEQ ID NO: 33            moltype = DNA   length = 23
FEATURE                  Location/Qualifiers
source                   1..23
                         mol_type = genomic DNA
                         organism = Homo sapiens
SEQUENCE: 33
ggagggaggg aaacagcccc agg                                              23

SEQ ID NO: 34            moltype = AA   length = 1375
FEATURE                  Location/Qualifiers
source                   1..1375
                         mol_type = protein
                         organism = Streptococcus canis
SEQUENCE: 34
MEKKYSIGLD IGTNSVGWAV ITDDYKVPSK KFKVLGNTNR KSIKKNLMGA LLFDSGETAE    60
ATRLKRTARR RYTRRKNRIR YLQEIFANEM AKLDDSFFQR LEESFLVEED KKNERHPIFG   120
NLADEVAYHR NYPTIYHLRK KLADSPEKAD LRLIYLALAH IIKFRGHFLI EGKLNAENSD   180
VAKLFYQLIQ TYNQLFEESP LDEIEVDAKG ILSARLSKSK RLEKLIAVFP NEKKNGLFGN   240
IIALALGLTP NFKSNFDLTE DAKLQLSKDT YDDDLDELLG QIGDQYADLF SAAKNLSDAI   300
LLSDILRSNS EVTKAPLSAS MVKRYDEHHQ DLALLKTLVR QQFPEKYAEI FKDDTKNGYA   360
GYVGADKKLR KRSGKLATEE EFYKFIKPIL EKMDGAEELL AKLNRDDLRR KQRTFDNGSI   420
PHQIHLKELH AILRRQEEFY PFLKENREKI EKILTFRIPY YVGPLARGNS RFAWLTRKSE   480
EAITPWNFEE VVDKGASAQS FIERMTNFDE QLPNKKVLPK HSLLYEYFTV YNELTKVKYV   540
TERMRKPEFL SGEQKKAIVD LLFKTNRKVT VKQLKEDYFK KIECFDSVEI IGVEDRFNAS   600
LGTYHDLLKI IKDKDFLDNE ENEDILEDIV LTLTLFEDRE MIEERLKTYA HLFDDKVMKQ   660
LKRRHYTGWG RLSRKLINGI RDKQSGKTIL DFLKSDGFAN RNFMQLIHDD SLTFKEEIEK   720
AQVSGQGDSL HEQIADLAGS PAIKKGILQT VKIVDELVKV MGHKPENIVI EMARENQTTT   780
KGLQQSRERK KRIEEGIKEL ESQILKENPV ENTQLQNEKL YLYYLQNGRD MYVDQELDIN   840
RLSDYDVDHI VPQSFIKDDS IDNKVLTRSV ENRGKSDNVP SEEVVKKMKN YWRQLLNAKL   900
ITQRKFDNLT KAERGGLSEA DKAGFIKRQL VETRQITKHV ARILDSRMNT KRDKNDKPIR   960
EVKVITLKSK LVSDFRKDFQ LYKVRDINNY HHAHDAYLNA VVGTALIKKY PKLESEFVYG  1020
DYKVYDVRKM IAKSEQEIGK ATAKRFFYSN IMNFFKTEVK LANGEIRKRP LIETNGETGE  1080
VVWNKEKDFA TVRKVLAMPQ VNIVKKTEVQ TGGFSKESIL SKRESAKLIP RKKGWDTRKY  1140
GGFGSPTVAY SILVVAKVEK GKAKKLKSVK VLVGITIMEK GSYEKDPIGF LEAKGYKDIK  1200
KELIFKLPKY SLFELENGRR RMLASAKELQ KANELVLPQH LVRLLYYTQN ISATTGSNNL  1260
GYIEQHREEF KEIFEKIIDF SEKYILKNKV NSNLKSSFDE QFAVSDSILL SNSFVSLLKY  1320
TSFGASGGFT FLDLDVKQGR LRYQTVTEVL DATLIYQSIT GLYETRTDLS QLGGD       1375

SEQ ID NO: 35            moltype = AA   length = 9
FEATURE                  Location/Qualifiers
source                   1..9
                         mol_type = protein
                         organism = Streptococcus gordonii
SEQUENCE: 35
LASAKELQK                                                              9

SEQ ID NO: 36            moltype = AA   length = 9
FEATURE                  Location/Qualifiers
source                   1..9
                         mol_type = protein
                         organism = Streptococcus pyogenes
SEQUENCE: 36
LASAGELQK                                                              9

SEQ ID NO: 37            moltype = AA   length = 9
FEATURE                  Location/Qualifiers
source                   1..9
                         mol_type = protein
                         organism = Streptococcus pyogenes
SEQUENCE: 37
LASAGVLQK                                                              9

SEQ ID NO: 38            moltype = AA   length = 9
FEATURE                  Location/Qualifiers
source                   1..9
                         mol_type = protein
                         organism = Streptococcus pyogenes
SEQUENCE: 38
LASARFLQK                                                              9

SEQ ID NO: 39            moltype = AA   length = 9
FEATURE                  Location/Qualifiers
source                   1..9
                         mol_type = protein
                         organism = Streptococcus canis
SEQUENCE: 39
LASATELQK                                                              9

SEQ ID NO: 40            moltype = AA   length = 19
```

```
FEATURE             Location/Qualifiers
source              1..19
                    mol_type = protein
                    organism = Streptococcus anginosus
SEQUENCE: 40
VGADKKLRKR KRSGKLATE                                                      19

SEQ ID NO: 41       moltype = AA  length = 7
FEATURE             Location/Qualifiers
source              1..7
                    mol_type = protein
                    organism = Streptococcus pyogenes
SEQUENCE: 41
IDGGASQ                                                                    7

SEQ ID NO: 42       moltype = AA  length = 17
FEATURE             Location/Qualifiers
source              1..17
                    mol_type = protein
                    organism = Streptococcus canis
SEQUENCE: 42
VGIGIKHRKR TTKLATQ                                                        17

SEQ ID NO: 43       moltype = DNA  length = 21
FEATURE             Location/Qualifiers
source              1..21
                    mol_type = genomic DNA
                    organism = Homo sapiens
SEQUENCE: 43
gataaatctg gtcttatttc c                                                   21
```

APPLICATIONS OF ENGINEERED STREPTOCOCCUS CANIS Cas9 VARIANTS ON SINGLE-BASE PAM TARGETS

RELATED APPLICATIONS

This application is a divisional of U.S. patent application Ser. No. 17/855,507, filed Jun. 30, 2022, now U.S. Pat. No. 11,697,808, issued Jul. 11, 2023, which is a divisional of U.S. patent application Ser. No. 16/689,071, filed Nov. 19, 2019, now U.S. Pat. No. 11,453,865, issued Sep. 27, 2022, which claims the benefit of U.S. Provisional Application Ser. No. 62/769,520, filed Nov. 19, 2018, the entire disclosures of which are herein incorporated by reference.

U.S. patent application Ser. No. 16/689,071 is also a continuation-in-part of U.S. patent application Ser. No. 16/136,238, filed Sep. 19, 2018, which claims the benefit of U.S. Provisional Application Ser. No. 62/560,630, filed Sep. 19, 2017, the entire disclosures of which are herein incorporated by reference.

INCORPORATION BY REFERENCE OF SEQUENCE LISTING XML

This application contains a Sequence Listing XML submitted under the provisions of 37 CFR 1.831(a) and herein incorporated by reference. The Sequence Listing XML includes, in XML format, the following file:
File name Creation Date Size in bytes
MIT1150.xml 7/11/2023 11:19 PM 43000

FIELD OF THE TECHNOLOGY

The present invention relates to genome editing and, in particular, to *Streptococcus* Cas9 orthologs having novel PAM specificity, along with variants and uses thereof.

BACKGROUND

Programmable Clustered Regularly Interspaced Short Palindromic Repeats (CRISPR) enzymes are powerful and versatile tools for genome editing. The RNA-guided DNA endonucleases (RGENs) of the CRISPR-Cas system, such as Cas9 [M. Jinek, K. Chylinski, I. Fonfara, M. Hauer, J. A. Doudna, et al., "A programmable dual-RNA-guided DNA endonuclease in adaptive bacterial immunity", Science 337, 816-821 (2012)] and Cpf1 (also known as Cas12a) [B. Zetsche, J. S. Gootenberg, O. O. Abudayyeh, I. M. Slaymaker, K. S. Makarova, et al., "Cpf1 is a Single RNA-Guided Endonuclease of a Class 2 CRISPR-Cas System", Cell 163, 759-771 (2015)], have been successfully harnessed for various genome editing and regulation applications [Sander, J. D. & Joung, J. K., "CRISPR-Cas systems for editing, regulating and targeting genomes", Nature Biotechnology 32, 347-355 (2014); Doudna, J. A. & Charpentier, "E. Genome editing. The new frontier of genome engineering with CRISPR-Cas9", Science 346, 1258096 (2014); L. S. Qi, M. H. Larson, L. A. Gilbert, J. A. Doudna, J. S. Weissman, et al., "Repurposing CRISPR as an RNA-Guided Platform for Sequence-Specific Control of Gene Expression", Cell 152, 1173-1183 (2013)], which has numerous implications in medicine, agriculture, bioenergy, food security, nanotechnology, and beyond [R. Barrangou, P. Horvath, "A decade of discovery: CRISPR functions and applications", Nat. Microbiol. 2, 17092 (2017)].

However, the range of targetable sequences for CRISPR endonucleases is limited by the need for a specific protospacer adjacent motif (PAM), which is determined by DNA-protein interactions, to immediately follow the DNA sequence specified by the single guide RNA (sgRNA) in order to access specific targets [Mojica, F. J., et al., "Short motif sequences determine the targets of the prokaryotic CRISPR defense system", Microbiology 155, 733-740 (2009); Shah, S. A., et al., "Protospacer recognition motifs: mixed identities and functional diversity", RNA Biology 10, 891-899 (2013); Jinek, M. et al., "A programmable dual-RNA-guided DNA endonuclease in adaptive bacterial immunity", Science 337, 816-821 (2012); Sternberg, S. H., et al., "DNA interrogation by the CRISPR RNA-guided endonuclease Cas9", Nature 507, 62-67 (2014); Zetsche, B., et al., "Cpf1 is a Single RNA-Guided Endonuclease of a Class 2 CRISPR-Cas System", Cell 163:3, 759-771 (2015); F. Jiang, K. Zhou, L. Ma, S. Gressel, J. A. Doudna, "A Cas9-guide RNA complex preorganized for target DNA recognition", Science 384:6242, 1477-1481 (2015)], which constrains the accessible space for position-specific genome editing applications, such as, but not limited to, base editing and homology-directed repair.

For example, the most widely used variant, *Streptococcus pyogenes* Cas9 (SpCas9), requires a guanine (G)-rich 5'-NGG-3' PAM sequence downstream of its RNA-programmed DNA target [Jinek, M. et al., "A programmable dual-RNA-guided DNA endonuclease in adaptive bacterial immunity", Science 337, 816-821 (2012); R. Barrangou, P. Horvath, "A decade of discovery: CRISPR functions and applications", Nat. Microbiol. 2, 17092 (2017); Mojica, F. J., et al., "Short motif sequences determine the targets of the prokaryotic CRISPR defense system", Microbiology 155, 733-740 (2009); Shah, S. A., et al., "Protospacer recognition motifs: mixed identities and functional diversity", RNA Biology 10, 891-899 (2013); Sternberg, S. H., et al., "DNA interrogation by the CRISPR RNA-guided endonuclease Cas9", Nature 507, 62-67 (2014); F. Jiang, K. Zhou, L. Ma, S. Gressel, J. A. Doudna, "A Cas9-guide RNA complex preorganized for target DNA recognition", Science 384: 6242, 1477-1481 (2015)], severely restricting position-specific genome editing applications, such as base editing [A. C. Komor, Y. B. Kim, M. S. Packer, J. A. Zuris, D. R. Liu, "Programmable editing of a target base in genomic DNA without double-stranded DNA cleavage", Nature 533, 420-424 (2016); N. M. Gaudelli, A. C. Komor, H. A. Rees, M. S. Packer, A. H. Badran, et al., "Programmable base editing of A•T to G•C in genomic DNA without DNA cleavage", Nature 551, 464-471 (2017)] and homology-directed repair [C. D. Richardson, G. J. Ray, M. A. DeWitt, G. L. Curie, J. E. Corn, "Enhancing homology-directed genome editing by catalytically active and inactive CRISPR-Cas9 using asymmetric donor DNA", Nat. Biotechnol. 34, 339-344 (2016)], which represent promising routes for effrctive therapeutics and biotechnologies. In applications that require targeting a precise position along DNA, the current sequence limitation imposed by the small set of known PAM motifs has constrained the impact of synthetic genome engineering efforts [Mojica, F. J., et al., "Short motif sequences determine the targets of the prokaryotic CRISPR defense system", Microbiology 155, 733-740 (2009); Jinek, M. et al., "A programmable dual-RNA-guided DNA endonuclease in adaptive bacterial immunity", Science 337, 816-821 (2012); Zetsche, B., et al., "Cpf1 is a Single RNA-Guided Endonuclease of a Class 2 CRISPR-Cas System", Cell 163:3, 759-771 (2015)].

To relax this constraint, additional Cas9 and Cas12a variants with distinct PAM motif requirements have been either discovered [F. A. Ran, L. Cong, W. X. Yan, D. A. Scott, J. S. Gootenberg, et al., "In vivo genome editing using

*Staphylococcus aureus* Cas9", Nature 520, 186-191 (2015); K. M. Esvelt, P. Mali, J. L. Braff, M. Moosburner, S. J. Yaung, et al., "Orthogonal Cas9 proteins for RNA-guided gene regulation and editing", Nat. Methods 520, 186-191 (2013); E. Kim, T. Koo, S. W. Park, D. Kim, K. Kim, et al., "In vivo genome editing with a small Cas9 orthologue derived from *Campylobacter jejuni*", Nat. Commun. 8, 14500 (2017); H. Hirano, J. S. Gootenberg, T. Horii, O. O. Abudayyeh, M. Kimura, et al., "Structure and Engineering of *Francisella novicida* Cas9", Cell 164, 950-961 (2016); L. B. Harrington, D. Paez-Espino, B. T. Staahl, J. S. Chen, E. Ma, et al., "A thermostable Cas9 with increased lifetime in human plasma", Nat. Commun. 8, 1424 (2017)] or engineered [H. Hirano, J. S. Gootenberg, T. Horii, O. O. Abudayyeh, M. Kimura, et al., "Structure and Engineering of *Francisella novicida* Cas9", Cell 164, 950-961 (2016); L. B. Harrington, D. Paez-Espino, B. T. Staahl, J. S. Chen, E. Ma, et al., "A thermostable Cas9 with increased lifetime in human plasma", Nat. Commun. 8, 1424 (2017); B. P. Kleinstiver, M. S. Prew, S. Q. Tsai, V. V. Topkar, N. T. Nguyen, et al., "Engineered CRISPR-Cas9 nucleases with altered specificities", Nature 523, 481-485 (2015); L. Gao, D. B. T. Cox, W. X. Yan, J. C. Manteiga, M. W Schneider, et al., "Engineered Cpf1 variants with altered specificities", Nat. Biotechnol. 35, 789-792 (2017); D. Ma, Z. Xu, Z. Zhang, X. Chen, X. Zeng, et al., "Engineer chimeric Cas9 to expand PAM recognition based on evolutionary information", Nat. Commun. 10, 560 (2019); B. P. Kleinstiver, A. A. Sousa, R. T. Walton, Y. E. Tak, J. T. Hsu, et al., "Engineered CRISPR-Cas12a variants with increased activities and improved targeting ranges for gene, epigenetic and base editing", Nat. Biotechnol. 37, 276-282 (2019)], in order to diversify the range of targetable DNA sequences.

Bioinformatics tools have been utilized to align CRISPR cassettes of numerous bacterial species with presumed protospacers in phage or other genomes. This mapping helps to infer and subsequently test PAM sequences of naturally occurring orthologs that possess useful properties, such as decreased size [Ran, F. A. et al., "In vivo genome editing using *Staphylococcus aureus* Cas9", Nature 520, 186-191 (2015); Kim, E. et al., "In vivo genome editing with a small Cas9 orthologue derived from *Campylobacter jejuni*", Nature Communications 8, 14500 (2017)] and thermostability [Harrington, L. et al., "A thermostable Cas9 with increased lifetime in human plasma", bioRxiv (2017)]. However, such analysis does not guarantee efficient activity, and must be followed by assays to validate PAMs. Alternatively, functionally efficient RGENs, such as SpCas9 and *Acidaminococcus* sp. Cas12a (AsCas12a), have been utilized as scaffolds for engineering to produce variants with altered PAM specificities [Kleinstiver, B. P. et al., "Engineered CRISPR-Cas9 nucleases with altered specificities", Nature 523, 481-485 (2015); Gao, L., et al., "Engineered Cpf1 variants with altered specificities", Nature Biotechnology 35, 789-792 (2017)], with measured success.

Recently, three groups have independently reduced the 5'-NGG-3' PAM specificity of SpCas9 to a single guanine (G) nucleotide, by employing phage-assisted continuous evolution (xCas9-3.7) [J. H. Hu, S. M. Miller, M. H. Geurts, W. Tang, L. Chen, et al., "Evolved Cas9 variants with broad PAM compatibility and high DNA specificity", Nature 556, 5763 (2018)], structure-guided rational design (SpCas9-NG) [H. Nishimasu, X. Shi, S. Ishiguro, L. Gao, S. Hirano, et al., "Engineered CRISPR-Cas9 nuclease with expanded targeting space", Science 361, 1259-1262 (2018)], and bioinformatics discovery pipelines (ScCas9) [P. Chatterjee, N. Jakimo, J. M. Jacobson, "Minimal PAM specificity of a highly similar SpCas9 ortholog", Science Advances 4:10 (2018)]. Together, these enzymes have increased the targetable DNA sequence space to nearly 50%.

While these three new tools represent an exciting expansion of targets for genome editing, they each possess shortcomings that limit their broad applicability to a subset of single G PAM sites. For example, SpCas9-NG demonstrates reduced efficiency on 5'-NGC-3' PAM targets [H. Nishimasu, X. Shi, S. Ishiguro, L. Gao, S. Hirano, et al., "Engineered CRISPR-Cas9 nuclease with expanded targeting space", Science 361, 1259-1262 (2018)], while ScCas9 is notably inefficient at modifying target sequences within different gene contexts [P. Chatterjee, N. Jakimo, J. M. Jacobson, "Minimal PAM specificity of a highly similar SpCas9 ortholog", Science Advances 4:10 (2018)]. Finally, xCas9-3.7 has been suggested to possess higher fidelity rather than broad PAM recognition [K. Hua, X. Tao, P. Han, R. Wang, J. K. Zhu, "Genome engineering in rice using Cas9 variants that recognize NG PAM sequences", Mol. Plant (2019); Z. Zhong, S. Stretenovic, Q. Ren, L. Yang, Y. Bao, et al., "Improving plant genome editing with high-fidelity xCas9 and non-canonical PAM-targeting Cas9-NG", Mol. Plant (2019)]. Thus, there is a critical need for continual improvement of these enzymes for genome editing purposes.

SUMMARY

ScCas9 variants according to the invention have more flexible targeting of 5'-NG-3' and 5'-NNG-3' genomic sequences than that of the first generation of single G editors. Specifically, these variants demonstrate broader editing capabilities in both nucleolytic and base editing contexts, as compared to the first generation of single G editors. The invention demonstrates a critical step towards full coverage of the genomic sequence space. Motifs were employed from closely-related orthologs to engineer and optimize ScCas9 to exhibit enhanced genome editing and higher fidelity. The engineered variants demonstrate superior activity within gene repression and nucleolytic contexts and possess effective base editing capabilities. Broad-targeting and efficient ScCas9 enzymes ("Sc+" and "Sc++") were engineered by utilizing evolutionary information from closely-related orthologs to generate two novel modifications to the original ORF. Taken together, these alterations enable Sc+ and Sc++ to possess enhanced editing capabilities in both bacterial and human cells, in comparison to SpCas9, xCas9-3.7, SpCas9-NG, and ScCas9. A preferred embodiment includes a high-fidelity variant of Sc++ for genome modification with improved specificity.

In one aspect, the invention includes an isolated, engineered *Streptococcus canis* Cas9 (ScCas9) protein with its PID being the PID amino acid composition of *Streptococcus pyogenes* Cas9 (SpCas9)-NG.

In another aspect, the invention includes an isolated, engineered ScCas9 protein having a threonine-to-lysine substitution mutation at position 1227 in its amino acid sequence (Sc+).

In yet another aspect, the invention includes an isolated, engineered ScCas9 protein having a threonine-to-lysine substitution mutation at position 1227 in its amino acid sequence and a substitution of residues ADKKLRKRSGKLATE [SEQ ID No: 4] in position 365-379 in the ScCas9 open reading frame, in addition to the T1227K substitution (Sc++).

In a further aspect, the invention includes CRISPR-associated DNA endonucleases with a PAM specificity of 5'-NG-3' or 5'-NNG-3'.

In yet a further aspect, the invention includes a method of altering expression of at least one gene product, comprising steps of introducing, into a eukaryotic cell containing and expressing a DNA molecule having a target sequence and encoding the gene product, an engineered, non-naturally occurring Clustered Regularly Interspaced Short Palindromic Repeats (CRISPR)— CRISPR-associated (Cas) (CRISPR-Cas) system comprising one or more vectors comprising: (a) a regulatory element, operable in a eukaryotic cell, operably linked to at least one nucleotide sequence encoding a CRISPR system guide RNA that hybridizes with the target sequence, and (b) a second regulatory element, operable in a eukaryotic cell, operably linked to a nucleotide sequence encoding at least one protein selected from the group comprising an isolated, engineered Streptococcus canis Cas9 (ScCas9) protein with its PID as the PID amino acid composition of SpCas9-NG, an isolated, engineered ScCas9 protein with its harboring a threonine-to-lysine substitution mutation at position 1227 in its amino acid sequence, an isolated, engineered ScCas9 protein with its harboring a threonine-to-lysine substitution mutation at position 1227 in its amino acid sequence in combination with a substitution of residues ADKKLRKRSGKLATE [SEQ ID No: 4] in position 365-379 in the ScCas9 open reading frame, and combinations thereof, wherein components (a) and (b) are located on same or different vectors of the system, whereby the guide RNA targets the target sequence and one or more of the proteins cleave the DNA molecule, whereby expression of the at least one gene product is altered, and wherein the proteins and the guide RNA do not naturally occur together.

BRIEF DESCRIPTION OF THE DRAWINGS

Other aspects, advantages and novel features of the invention will become more apparent from the following detailed description of the invention when considered in conjunction with the accompanying drawings, wherein:

FIG. 1 depicts the global pairwise sequence alignment of Streptococcus pyogenes Cas9 (SpCas9) [SEQ ID NO: 26] and Streptococcus canis Cas9 (ScCas9) [SEQ ID NO: 27].

FIGS. 6-8 illustrate ScCas PAM specificity in human cells, wherein:

FIG. 6 depicts an example T7E1 analysis of indels produced at VEGFA loci with indicated PAM sequences.

FIG. 7 is a graph depicting a quantitative analysis of T7E1 products.

FIG. 8 is a graph depicting example results from ScCas9-mediated A-*G Base Editing.

FIGS. 9-12 illustrate ScCas9 performance as a genome editing tool, wherein:

FIG. 9 is a graph of results from quantitative analysis of T7E1 products for indicated genomic on-target (VEGFA site 3 [SEQ ID NO: 28], FANCF site 2 [SEQ ID NO: 29], DNMT1 site 4 [SEQ ID NO: 30]) and off-target (VEGFA site 3 [SEQ ID NO: 31], FANCF site 2 [SEQ ID NO: 32], DNMT1 site 4 [SEQ ID NO: 33]) editing.

FIG. 10 is an efficiency heatmap of a mismatch tolerance assay.

FIG. 11 is a dot plot of on-target modification percentages at various gene targets for indicated PAM, as assessed by the T7E1 assay.

FIG. 12 depicts genomic base editing characterization.

FIGS. 13 and 14 depict the relationship of ScCas9 to other Streptococcus orthologs, wherein:

FIG. 13 depicts PAM binding enrichment on a ' PAM library of ScCas9-like SpCas9 variants.

FIG. 14 shows a FACS analysis of binding at an 5'-NGG-3' PAM.

FIGS. 18-20 illustrate aspects of the engineering and PAM determination of ScCas9 variants according to the invention, wherein:

FIG. 18 depicts the amino acid sequence of ScCas9++ [SEQ ID NO: 34], showing the T1227K mutation derived from Streptococcus gordonii [SEQ ID NO: 35] (shown compared to SpCas9 [SEQ ID NO: 36], Xcas9.3.7 [SEQ ID NO: 37], SpCas9-NG [SEQ ID NO: 38], and ScCas9 [SEQ ID NO: 39]) and the novel loop structure from Streptococcus anginosus [SEQ ID NO: 40] (shown compared to SpCas9 [SEQ ID NO: 41] and ScCas9 [SEQ ID NO: 42]) that harbors an additional lysine residue and a flexible "SG" motif, according to an aspect of the invention.

FIG. 20 is a PAM binding enrichment visualization, wherein PAM profiles are represented by DNA chromatograms via amplification of PAM region following plasmid extraction of GFP-positive E. coli cells and subsequent Sanger sequencing.

FIGS. 21-23 illustrate aspects of the genome editing capabilities of engineered ScCas9 variants according to the invention, wherein:

FIG. 21 is a graph depicting a quantitative analysis of nucleolytic editing with single G PAM Cas9 variants, according to one aspect of the invention.

FIG. 22 illustrates a quantitative analysis of C→T base editing with ScCas9+BE3, according to one aspect of the invention.

FIG. 23 is an efficiency heatmap of a mismatch tolerance assay on a genomic target, according to one aspect of the invention, wherein quantified indel frequencies are exhibited for each labeled single or double mismatch in the sgRNA sequence for the indicated Cas9 variant.

DETAILED DESCRIPTION

Figure 2:
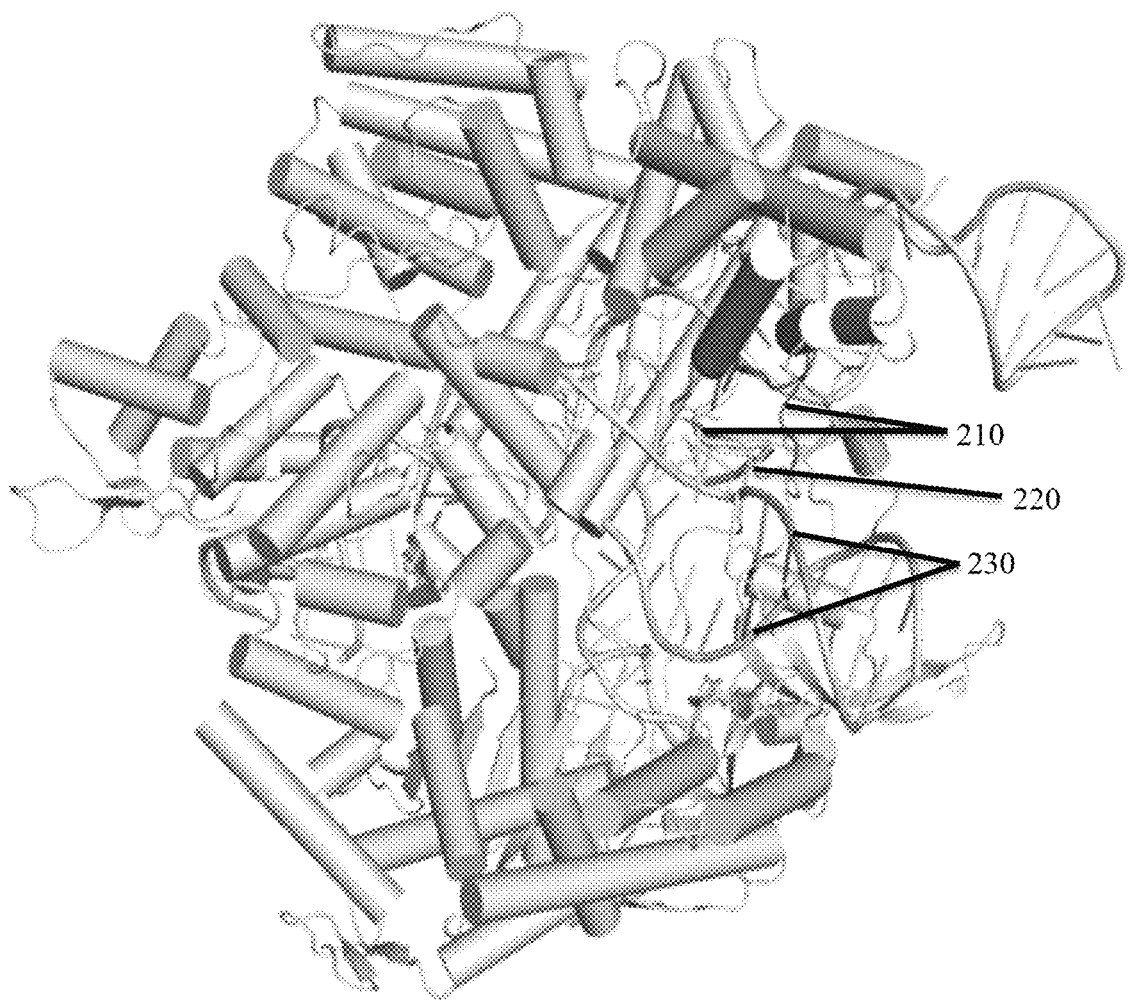
FIG. 2 illustrates the DNA-interacting loop domain within ScCas9, and other Cas9 orthologs, demonstrating that this loop forms expected sequence unspecific contacts with the negatively-charged phosphate backbone of the target DNA strand.

In one aspect, the invention is an addition to the family of CRISPR-Cas9 systems repurposed for genome engineering and regulation applications. Specifically, the invention comprises the usage of *Streptococcus canis* Cas9 (ScCas9) endonuclease in complex with guide RNA, consisting of an identical non-target-specific sequence to that of the guide RNA SpCas9, for specific recognition and activity on a DNA target immediately upstream of either an "NNGT" or "NNNGT" PAM sequence, promoting new flexibility in target selection. In a further aspect, the invention is a novel DNA-interacting loop domain within ScCas9, and other Cas9 orthologs, such as those from *Streptococcus gordonii* (Uniprot A0A134D9V8) and *Streptococcus angionosis* (Uniprot F5U0T2), that may facilitate a divergent PAM sequence from the canonical "NGG" PAM of SpCas9.

As previously described, the application of CRISPR-Cas9 has been hampered by the inaccessibility of genomic sequences, largely due to the PAM restriction. The recent discoveries of ScCas9, xCas9-3.7, and SpCas9-NG, all reporting to possess single G PAM specificity, significantly increased the targetable space, potentially allowing for expanded base editing activities, more efficient homology-directed repair, and denser screening platforms. As all have been shown to possess limitations, however, including inefficient targeting of certain single G PAM sequences, the present invention addresses this problem by engineering ScCas9 to possess increased efficiency and broader targeting capabilities, by utilizing sequence information from engineered Cas9 variants and uncharacterized *Streptococcus* Cas9 orthologs. Sc+ and Sc++ nucleases outperform SpCas9, xCas9-3.7, SpCas9-NG, and ScCas9 as genome editing tools, and can thus be harnessed for various applications, including base editing. Furthermore, due to high sequence homology of ScCas9 and SpCas9, previous modifications made to SpCas9, such as high-fidelity mutations [C. A. Vakulskas, D. P. Dever, G. R. Rettig, R. Turk, A. M. Jacobi, et al., "A high-fidelity Cas9 mutant delivered as a ribonucleoprotein complex enables efficient gene editing in human hematopoietic stem and progenitor cells", Nat. Medicine 24, 1216-1224 (2018)], can be ported into these engineered variants for improved functionality. Sc+ and Sc++, with their broad targeting range and high genome editing efficiency, will hopefully serve as platforms toward the goals of versatile genome engineering and eventual access to every sequence in the entire genome.

Identification of SpCas Homologs

While numerous Cas9 homologs have been sequenced, only a handful of *Streptococcus* orthologs have been characterized or functionally validated. To explore this space, all *Streptococcus* Cas9 protein sequences from UniProt [The UniProt Consortium, "UniProt: the universal protein knowledgebase", Nucleic Acids Res. 45, D158-D169 (2017)] were curated, global pairwise alignments using the BLOSUM62 scoring matrix [S. Henikoff, J. G. Henikoff, "Amino acid substitution matrices from protein blocks", Proc. Natl. Acad. Sci. 89, 10915-10919 (1992] were performed, and percent sequence homology to SpCas9 was calculated.

As shown in Table 1, a bioinformatics workflow to identify the PAM specificity of ScCas9 in silico involves the alignment of the spacer sequences within the CRISPR cassette of *Streptococcus canis* with potential protospacers found within the phage and/or other genome databases. As the PAM lies immediately adjacent to the protospacer sequence, these sequences can be conglomerated and weighted based on the number of mismatches to infer bases that are overrepresented at each position [Ran, F. A. et al., "In vivo genome editing using *Staphylococcus aureus* Cas9", Nature 520, 186-191 (2015); Crooks, G. E. et al. "WebLogo: a sequence logo generator", Genome Res. 14, 1188-1190 (2004)].

TABLE 1

| *S. canis* Spacer (5' to 3') | Protospacer Source | Adjacent Motif (5' to 3') |
|---|---|---|
| CCGCTGACAACATTGTTGGC [SEQ ID No: 1] | *Streptococcus pyogenes* MGAS2096 (phage protein) | CAGTTAAT |
| TTTCAATGGTAAGATCATTC [SEQ ID No: 2] | *Streptococcus* phage P9 | ATGTTGAA |
| GTTTACGCTCATCAGATAGA [SEQ ID No: 3] | *Streptococcus* phage P9 | AAGTCTAA |

An orthologous Cas9 protein from *Streptococcus canis*, ScCas9 (UniProt I7QXF2) was found to possess 89.2% sequence similarity to Sp-Cas9. Despite such homology, ScCas9 prefers a more minimal 5'-NNG-3' PAM. To explain this divergence, two significant insertions were identified within its open reading frame (ORF) that differentiate ScCas9 from SpCas9 and contribute to its PAM-recognition flexibility. ScCas9 can efficiently and accurately edit genomic DNA in mammalian cells.

Figure 1:
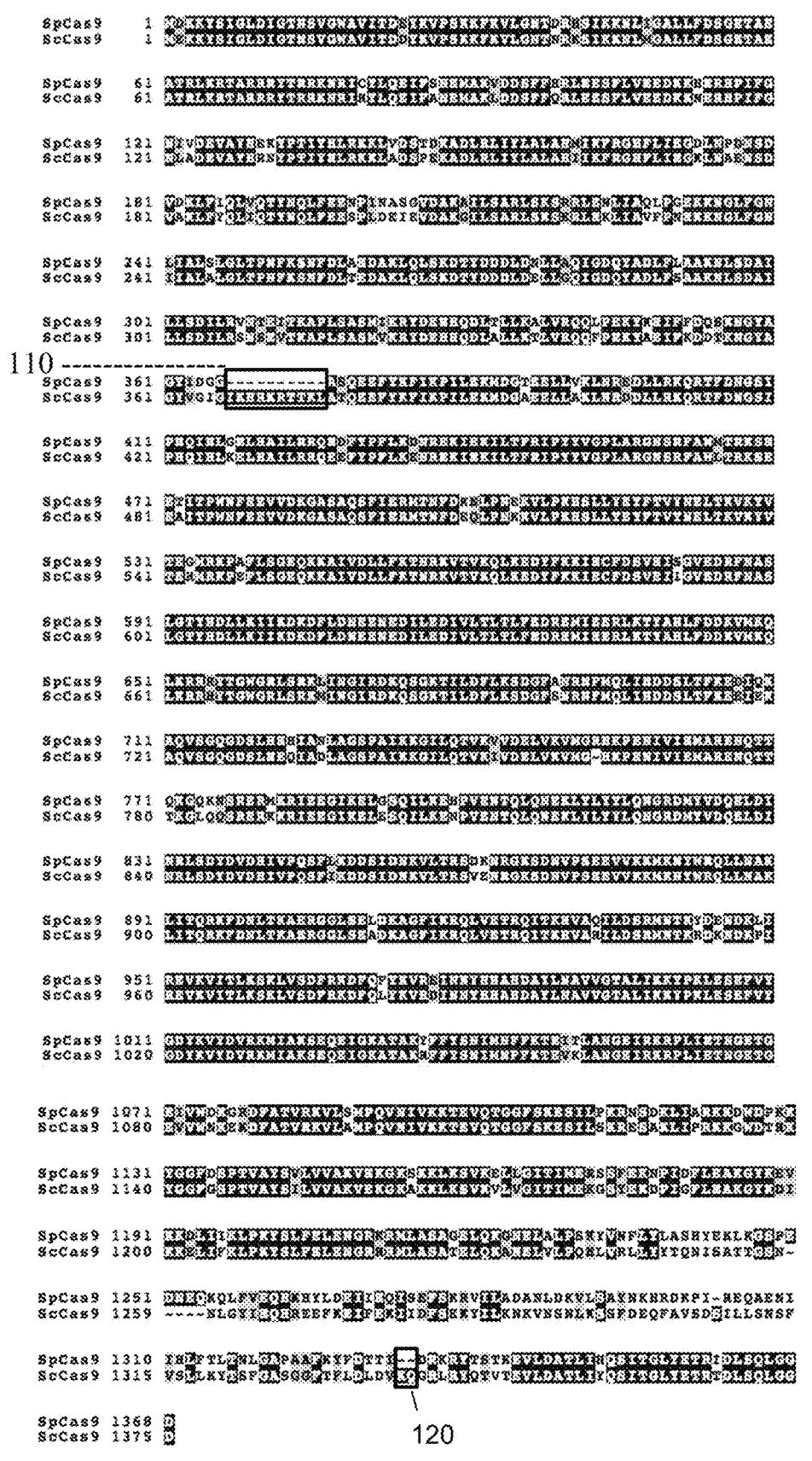

From the calculations, the Cas9 from *Streptococcus canis* (ScCas9) stood out, not only due to its remarkable sequence homology (89.2%) to SpCas9, but also because of the positive-charged insertion of 10 amino acids within the highly-conserved REC3 domain, in positions 367-376. FIG. 1 depicts the global pairwise amino acid sequence alignment of *Streptococcus pyogenes* Cas9 (SpCas9) (Uniprot Q99ZW2) and ScCas9 (Uniprot I7QXF2). As seen in FIG. 1, despite sharing 89.2% sequence homology to SpCas9, ScCas9 contains two notable insertions, one positive-charged insertion 110 in the REC domain (367-376) and another KQ insertion 120 in the PAM-interacting domain (1337-1338), as indicated. The 10-residue loop, not found in SpCas9, consists of 8 positively charged amino acids (KHRKRTTK) flanked by two neutral amino acids (I and L).

Exploiting both of these properties, the insertion was modeled within the corresponding domain of PDB 4008 [H.

Nishimasu, F. A. Ran, P. D. Hsu, S. Konermann, S. I. Shehata, et al., "Crystal structure of Cas9 in complex with guide RNA and target DNA", Cell 156, 935-949 (2014] and, when viewed in PyMol, it formed a "loop"-like structure, of which several of its positive-charged residues come in close proximity with the target DNA near the PAM. FIG. 2 illustrates the DNA-interacting loop domain within ScCas9, and other Cas9 orthologs, demonstrating that this loop forms expected sequence unspecific contacts with the negatively-charged phosphate backbone of the target DNA strand. Due to the absence of a crystal structure of ScCas9, the in silico insertion of this amino acid motif into PDB 4OO8, which depicts SpCas9 in complex with guide RNA and target DNA [Nishimasu, H. et al., "Crystal structure of Cas9 in complex with guide RNA and target DNA", Cell 156, 935-949 (2014)], demonstrates that this loop forms expected sequence unspecific contacts with the negatively-charged phosphate backbone of the target DNA strand. As shown in FIG. 2, the novel REC motif is inserted into PDB 4OO8. The 367-376 insertion demonstrates a loop-like structure 210. Several of its positive-charged residues 220 come in close proximity to the target DNA near the PAM 230. In a preferred embodiment of the invention, the novel loop domain can be inserted into the open reading frame (ORF) of SpCas9, and all characterized Cas9 orthologs, such as *Streptococcus thermophilus* (Uniprot G3ECR1), and other CRISPR endonucleases, such as Cpf1 (Uniprot U2UMQ6 and A0Q7Q2), for the generation of altered PAM specificities through increased protein-DNA interactions.

Figure 3:
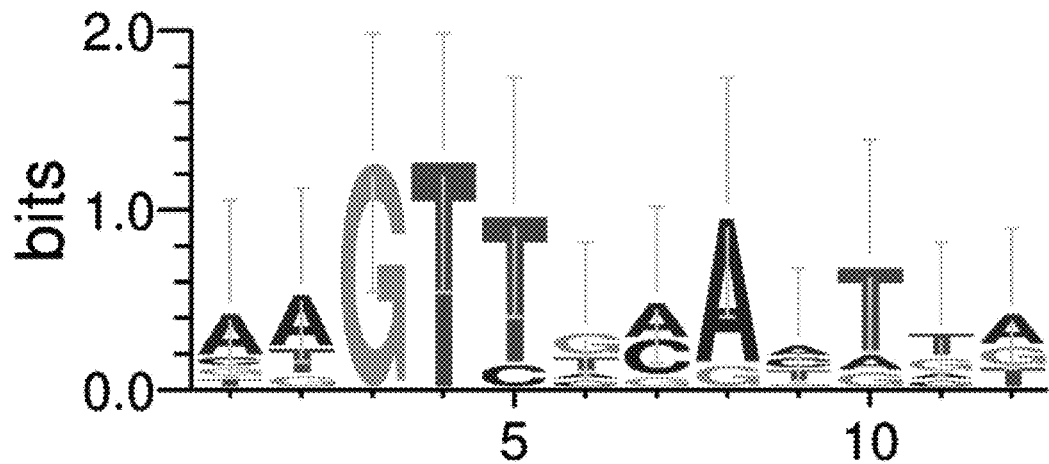
FIG. 3 depicts a WebLogo for sequences found at the 3' end of protospacer targets identified in plasmid and viral genomes using Type II spacer sequences within Streptococcus canis as BLAST queries.

An additional insertion of two amino acids (KQ) was identified immediately upstream of the two critical arginine residues necessary for PAM binding [C. Anders, K. Bargsten, M. Jinek, "Structural plasticity of PAM recognition by engineered variants of the RNA-guided endonuclease Cas9", Mol. Cell 61, 895-902 (2016)], in positions 1337-1338 (FIG. 1). It was hypothesized that these insertions may affect the PAM specificity of this enzyme. To support this prediction, the PAM was computationally characterized for ScCas9, by first mapping spacer sequences from the Cas9-associated type II CRISPR loci in the *Streptococcus canis* genome [T. Lef ebure, V. P. Richards, P. Lang, P. Pavinski-Bitar, M. J. Stanhope, "Gene Repertoire Evolution of *Streptococcus pyogenes* Inferred from Phylogenomic Analysis with *Streptococcus canis* and *Streptococcus dysgalactiae*", PLOS ONE 7, e37607 (2012)] to viral and plasmid genomes using BLAST [S. F. Altschul, W. Gish, W. Miller, E. W. Myers, D. J. Lipman, "Basic Local Alignment Search Tool", Jour. of Mol. Biol. 215, 403-410 (1990)], extracting the sequences 3' to the mapped protospacers, and subsequently a WebLogo [G. E. Crooks, G. Hon, J. M. Chandonia, S. E. Brenner, "WebLogo: A Sequence Logo Generator", Genome Res. 14, 1188-1190 (2004)] representation of the aligned PAM sequences was generated. FIG. 3 is a WebLogo for sequences found at the 3' end of protospacer targets identified in plasmid and viral genomes using Type II spacer sequences within *Streptococcus canis* as BLAST queries.

Analysis suggested an 5'-NNGTT-3' PAM. As FIG. 3 indicates, the sequence logo representing the motifs adjacent to three protospacers complementary to spacers in the *Streptococcus canis* genomic CRISPR cassettes demonstrates a strong preference for guanine (G) at the third position and a thymine (T) at the fourth position. Furthermore, an adenine (A) at position 7 is represented in all three protospacer PAMs, but is a sufficient distance away from the targeting sequence to be critical for Cas9 binding. Intrigued by these novel motifs and motivated by the potentially reduced specificity at position 2 of the PAM sequence, ScCas9 was selected as a candidate for further PAM characterization and engineering.

Determination of PAM Sequences Recognized by ScCas9

Due to the relatively low number of protospacer targets, the PAM binding sequence of ScCas9 was validated utilizing an existent positive selection bacterial screen based on GFP expression conditioned on PAM binding, termed PAM-SCANR [R. T. Leenay, K. R. Maksimchuk, R. A. Slotkowski, R. N. Agrawal, A. A. Gomaa, et al., "Identifying and Visualizing Functional PAM Diversity across CRISPR-Cas Systems", Mol. Cell 62, 137-147 (2016)]. A plasmid library containing the target sequence followed by a randomized 5'-NNNNNNNN-3' (8N) PAM sequence was bound by a nuclease-deficient ScCas9 (and dSpCas9 as a control) and an sgRNA both specific to the target sequence and general for SpCas9 and ScCas9, allowing for the repression of lad and expression of GFP. Plasmid DNA from FACS-sorted GFP-positive cells and pre-sorted cells were extracted and amplified, and enriched PAM sequences were identified by Sanger sequencing, and visualized utilizing DNA chromatograms. The results provided initial evidence that ScCas9 can bind to the minimal 5'-NNG-3' PAM, distinct to that of SpCas9's 5'-NGG-3'.

Figure 4:
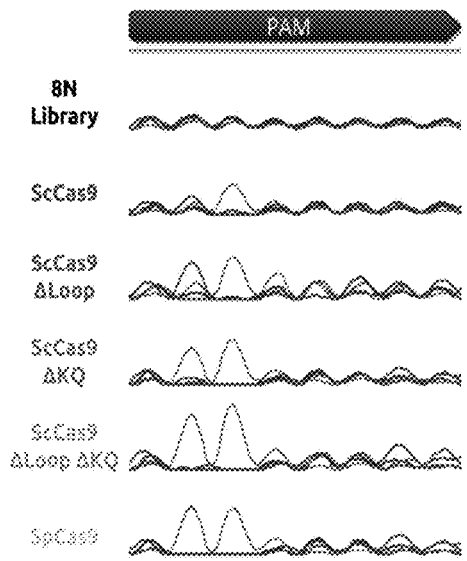
FIG. 4 illustrates PAM determination of engineered ScCas9 variants by showing PAM binding enrichment on a 5'-NNNNNNNN-3' (8N) PAM library.
Figure 5:
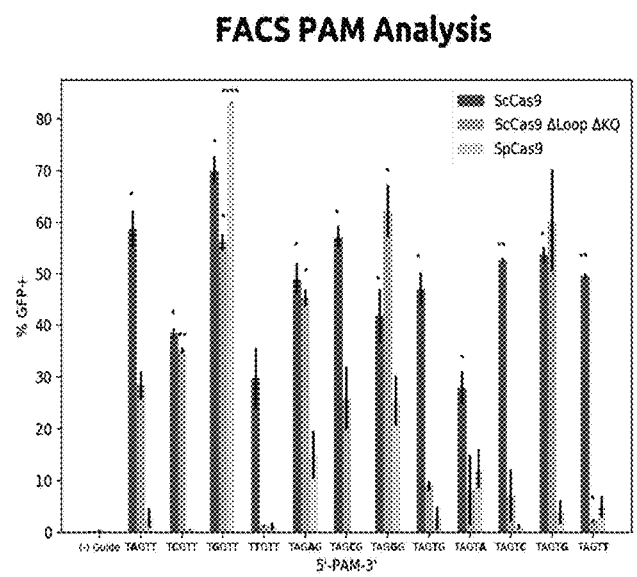
FIG. 5 is a graph illustrating an examination of PAM preference for ScCas9.

FIGS. 4 and 5 depict aspects of PAM determination of engineered ScCas9 variants. FIG. 4 illustrates PAM binding enrichment on a 5'-NNNNNNNN-3' (8N) PAM library. PAM profiles are represented by Sanger sequencing chromatograms via amplification of PAM region following plasmid extraction of GFP+*E. coli* cells.

The previously described insertions may contribute to the flexibility permitting ScCas9 to bind to the minimal 5'-NNG-3' PAM, distinct to that of SpCas9's 5'-NGG-3'. ScCas9 was engineered to remove either insertion or both, and subjected these variants to the same screen. Only removing the loop (ScCas9 Δ367-376 or ScCas9 ΔLoop) extended the PAM of ScCas9 to 5'-NAG-3', with reduced specificity for C and G at position 2, while only removing the KQ insertion (ScCas9 Δ1337-1338 or ScCas9 ΔKQ), reverted its specificity to a more 5'-NGG-3'-like PAM, with reduced specificity for A at position 2 (FIG. 4). Finally, the most SpCas9-like variant, where both insertions are removed (ScCas9 Δ367-376 Δ1337-1338 or ScCas9 ΔLoop ΔKQ), expectedly reverted its specificity back to 5'-NGG-3' (FIG. 4). Thus, from a functional perspective, these insertions operate in tandem to reduce the specificity of ScCas9 from the canonical 5'-NGG-3' PAM to a more minimal 5'-NNG-3'.

To confirm the results of the library assay and to rule out limiting downstream requirements, the minimal PAM requirements of ScCas9 were elucidated by utilizing fixed PAM sequences. The PAM library was replaced with individual PAM sequences, which were varied at positions 2, 4, and 5 to test each possible base. The results demonstrate that while ScCas9 exhibits no clear additional base dependence, with activity for all base iterations at each position, ScCas9 ΔLoop ΔKQ demonstrates significant binding at 5'-NGG-3' PAM sequences and at some, but not all, 5'-NNGNN-3' motifs, indicating an intermediate PAM specificity between that of SpCas9 and ScCas9.

FIG. 5 is a graph illustrating an examination of PAM preference for ScCas9. For individual PAMs, all four bases were iterated at a single position (2, 4, and 5). Each PAM-containing plasmid was electroporated in duplicates, subjected to FACS analysis, and gated for GFP expression. Subsequently, GFP expression levels were averaged. Standard deviation was used to calculate error bars and statistical significance analysis was conducted using a two-tailed Student's t-test as compared to the negative control.

To confirm an expected PAM sequence of "NNGT", a bacterial assay based upon lad promoter repression of GFP expression, employing 4 nucleotide libraries of PAM sequences upstream of lad, was utilized [Leenay, R. T. et al., "Identifying and visualizing functional PAM diversity across CRISPR-Cas systems", Mol. Cell 62, 137-147 (2016)]. The library-containing plasmids were co-electroporated with a gRNA plasmid and a nuclease-activity deficient ScCas9 (dScCas9) plasmid, all expressing different antibiotic resistance cassettes. Transformants were plated on triple antibiotic-containing LB agar plates, and GFP positive colonies were subsequently selected and screened.

Sequencing results confirmed that ScCas9 prefers an "NNGT" PAM, but can also tolerate a "NNNGT" PAM, indicating both potential conformational flexibility and strict sequence constraints of the ScCas9 PAM interacting domain (PID). No preference for A was observed at position 7. While various length PAMs with diverse sequences have either been discovered or engineered, this invention, with a PAM specificity of "NNGT" or "NNNGT", different than any known Cas9 variant [Karvelis, T. et al., "Methods for decoding Cas9 protospacer adjacent motif (PAM) sequences: A brief overview", Methods 121-122, 3-6 (2017)] and unable to be engineered from wild-type SpCas9 [Kleinstiver, B. P. et al., "Engineered CRISPR-Cas9 nucleases with altered specificities", Nature 523, 481-485 (2015)] or Cpf1 [Gao, L., et al., "Engineered Cpf1 variants with altered specificities", Nature Biotechnology 35, 789-792 (2017)], augments the list of potential genomic sites that can be targeted by the CRISPR system with high specificity and fidelity in a variety of cell types.

Additionally, there is a two amino acid insertion (KQ) at positions 1328 and 1329, immediately upstream of the two arginine (R) residues critical for PAM binding of Cas9. It is likely that this insertion shifts the length and alters the specificity of the PAM adjacent to the target sequence. A preferred embodiment of this invention enables both the insertion of the KQ motif one amino acid upstream of the first critical arginine residue in SpCas9 to alter its PAM specificity, as well as the removal of the KQ motif in ScCas9 for a similar purpose. Sufficient sequence, and potentially structural, differences from SpCas9 in its PAM interacting domain (PID) further enable exploration of a directed evolution phase space that SpCas9 may not be able to access, through random mutagenesis or rational design, which may also lead to expanded PAM specificities for ScCas9. These engineered PIDs of ScCas9 can be swapped with the PID of SpCas9 to further augment and alter its PAM specificities as well.

Further, due to the high degree of homology between SpCas9 and ScCas9, the propensity to cleave similar, but mismatched, sequences to the intended target is expected to be very similar for both wild-type endonucleases. Much work has been done to characterize and engineer mutations that destabilize strand displacement at mismatched substrates by weakening sequence dependent interactions between Cas9 and DNA (K848A, K1003A, R1060A [Slaymaker, I., et al., "Rationally engineered Cas9 Nucleases with improved specificity", Science 351, 84-88 (2016)] or N497A, R661A, Q695A, Q926A [Kleinstiver, B. P., et al., "High-fidelity CRISPR-Cas9 nucleases with no detectable genome-wide off-target effects", Nature 529, 490-495 (2016)]), and govern mismatch sensing in non-catalytic domains of Cas9 (N692A, M694A, Q695A, H698A) [Chen, J. S. et al. "Enhanced proofreading governs CRISPR-Cas9 targeting accuracy", bioRxiv (2017)]. In a preferred embodiment of this invention, these residue-specific mutations that decrease off-target activity while maintaining robust on-target nuclease activity can be applied to the ORF of ScCas9 to generate a hyper-accurate ScCas9 endonuclease.

For in vitro and in vivo applications, the invention is compatible with existing delivery methods used for other CRISPR-Cas9 systems including, but not limited to, electroporation, lipofection, viral infection, and nanoparticle injection. Embodiments can co-deliver the invention as a coding nucleic acid or protein, along with a gRNA. Components can also be stably expressed in cells.

Assessment of ScCas9 PAM Specificity in Human Cells

The PAM specificity of ScCas9 was compared to SpCas9 in human cells by co-transfecting HEK293T cells with plasmids expressing these variants along with sgRNAs directed to a native genomic locus (VEGFA) with varying PAM sequences. Editing efficiency was first tested at a site containing an overlapping PAM (5'-GGGT-3'). After 48 hours post-transfection, gene modification rates, as detected by the T7E1 assay, demonstrated comparable editing activities of SpCas9, ScCas9, and ScCas9 ΔLoop ΔKQ. Additionally sgRNAs to sites with various non-overlapping 5'-NNGN-3' PAM sequences were constructed. While SpCas9's cleavage activity was impaired at other non-5'-NGG-3' sequences (FIGS. 6 and 7) [P. D. Hsu, D. A. Scott, J. A. Weinstein, F. A. Ran, S. Konermann, et al., "DNA targeting specificities of RNA-guided Cas9 nucleases", Nat. Biotechnol. 31, 827-832 (2013)], ScCas9 maintained comparable activity to that of SpCas9 on its 5'-NGG-3' target across all tested targets with 5'-NNGN-3' PAM sequences.

Figure 6:
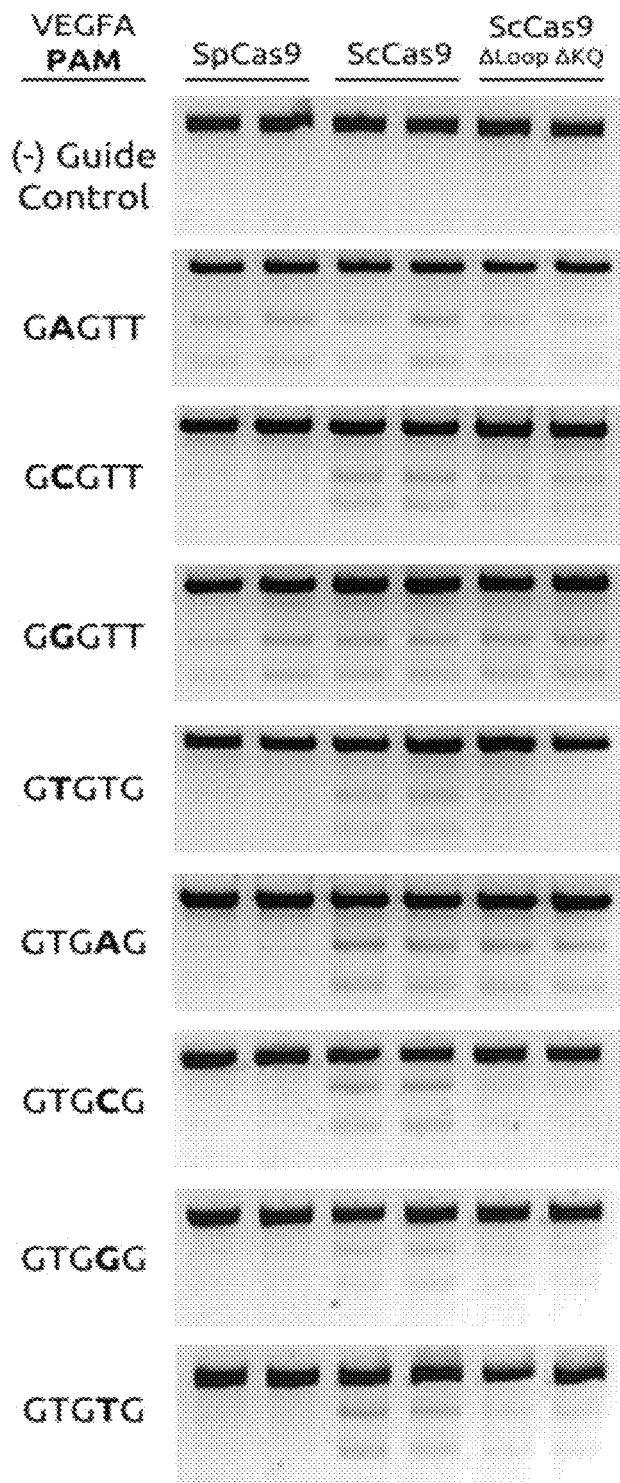
Figure 7:
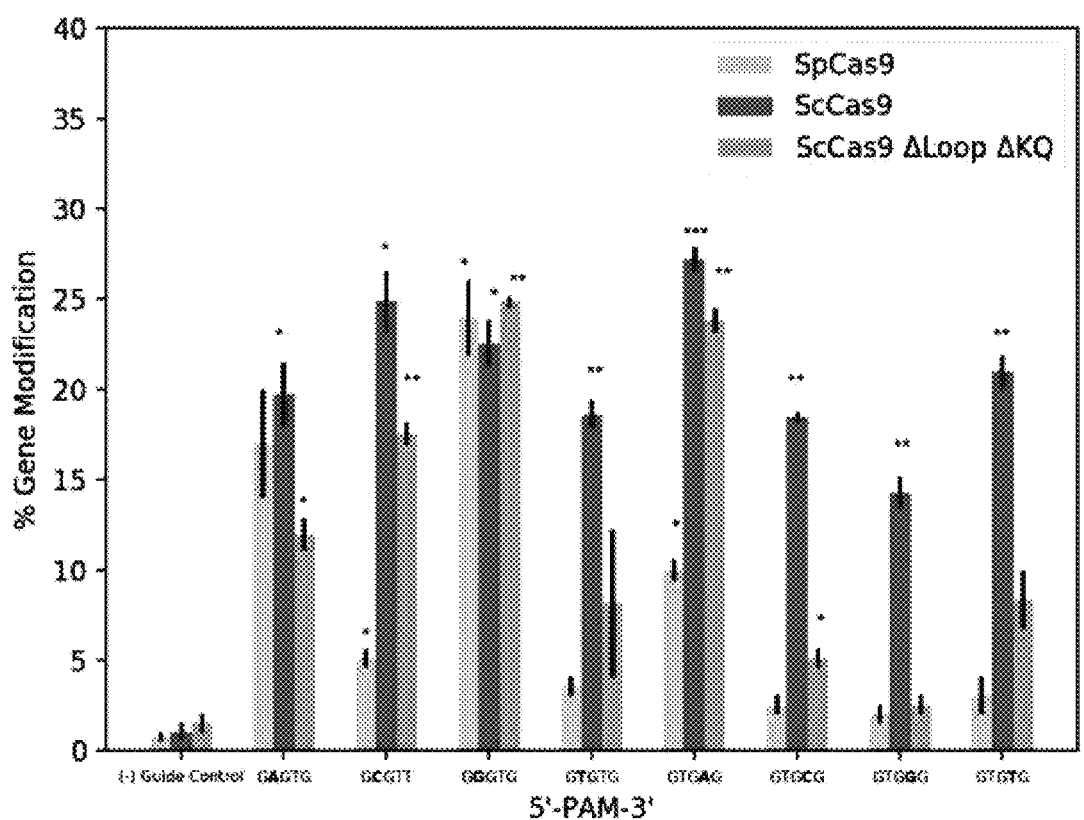

FIG. 6 depicts a T7E1 analysis of indels produced at VEGFA loci with indicated PAM sequences. The Cas9 used is indicated above each lane. All samples were performed in biological duplicates. As a background control, SpCas9, ScCas9, and ScCas9 ΔLoop ΔKQ were transfected without targeting guide RNA vectors. FIG. 7 is a graph depicting an example quantitative analysis of T7E1 products. Unprocessed gel images were quantified by line scan analysis using Fiji [J. Schindelin, I. Arganda-Carreras, E. Frise, V. Kaynig, M. Longair, et al., "Fiji: an open-source platform for biological-image analysis", Nat. Methods 9, 676-682 (2012], the total intensity of cleaved bands were calculated as a fraction of total product, and percent gene modification was calculated. All samples were performed in duplicates and quantified modification values were averaged. Standard deviation was used to calculate error bars and statistical significance analysis was conducted using a two-tailed Student's t-test as compared to the negative control.

Consistent with the bacterial data, ScCas9 ΔLoop ΔKQ was able to cleave at the 5'-NGG-3' target, along with significant activity on the 5'-NNGA-3' target, with reduced gene modification levels at all other 5'-NNGN-3' targets (FIGS. 6 and 7). Overall, these results verify that ScCas9 can serve as an effective alternative to SpCas9 for genome editing in mammalian cells, both at overlapping 5'-NGG-3' and more minimal 5'-NNGN-3' PAM sequences.

Figure 8:
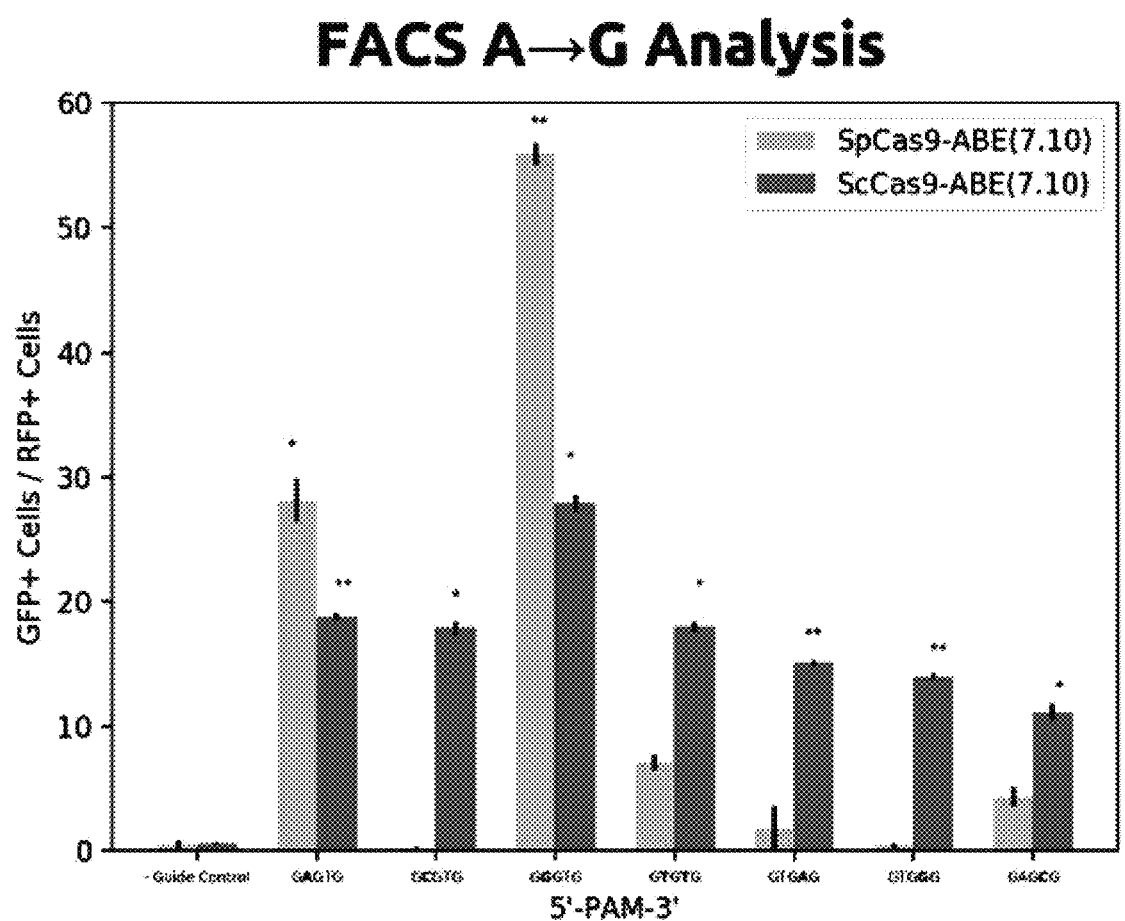

The PAM specificity of ScCas9 base editors was assessed by using a synthetic Traffic Light Reporter (TLR) [M. T. Certo, B. Y. Ryu, J. E. Annis, M. Garibov, J. Jarjour, et al., "Tracking genome engineering outcome at individual DNA breakpoints", Nat. Methods 8, 671-676 (2011)] plasmid, containing an early stop codon upstream of a GFP ORF and downstream of an mCherry ORF. Successful A-*G base editing using the ABE(7.10) architecture, as described in Gaudelli, et al. [N. M. Gaudelli, A. C. Komor, H. A. Rees, M. S. Packer, A. H. Badran, et al., "Programmable base editing of A·T to G·C in genomic DNA without DNA cleavage", Nature 551, 464-471 (2017)], converts an early, in-frame TAG stop codon to a TGG tryptophan codon, thus restoring GFP expression. After gating cells based on mCherry expression, significant base editing efficiency was observed at all 5'-NNGN-3' target PAM sequences for ScCas9-ABE(7.10), as compared to the SpCas9-ABE(7.10) architecture, which only demonstrates significant A→G conversion on the standard 5'-NGG-3' and tolerated 5'-NAG-3' motifs in this assay). FIG. 8 is a graph depicting example results from ScCas9-mediated A→G Base Editing. GFP+ cells were calculated as a percentage of mCherry+ cells for indicated PAM sequences using the Traffic Light Reporter [M. T. Certo, B. Y. Ryu, J. E. Annis, M. Garibov, J. Jarj our, et al., "Tracking genome engineering outcome at individual DNA breakpoints", Nat. Methods 8, 671-676 (2011)] with an early stop codon. All samples were performed in duplicates and quantified percentages were averaged. Standard deviation was used to calculate error bars and statistical significance analysis was conducted using a two-tailed Student's t-test.

Off-Target Analysis of ScCas9

The accuracy of this enzyme was evaluated in comparison to SpCas9. Previous genome-wide analysis of SpCas9 targeting accuracy was utilized to select three genomic targets (VEGFA site 3, FANCF site 2, and DNMT1 site 4) that possess multiple off-target sites on which SpCas9 demonstrates activity [S. Q. Tsai, Z. Zheng, N. T. Nguyen, M. Liebers, V. V. Topkar, et al., "GUIDE-seq enables genome-wide profiling of off-target cleavage by CRISPR-Cas nucleases", Nat. Biotechnol. 33, 187-197 (2015)]. Each of these three sites additionally possesses a single off-target that has been particularly difficult to mediate via engineering of high-fidelity Cas9 variants [I. M. Slaymaker, L. Gao, B. Zetsche, D. A. Scott, W. X. Yan, et al., "Rationally engineered Cas9 Nucleases with improved specificity", Science 351, 84-88 (2016); B. P. Kleinstiver, V. Pattanayak, M. S. Prew, S. Q. Tsai, N. T. Nguyen, et al., "High-fidelity CRISPR-Cas9 nucleases with no detectable genome-wide off-target effects", Nature 529, 490-495 (2016); J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)]. ScCas9's activity was analyzed on these off-targets. After co-transfection of sgRNAs to the three aforementioned sites alongside both SpCas9 and ScCas9, genomic DNA flanking both the on-target and difficult off-target sequences was amplified to assess their genome modification activities.

Figure 9:
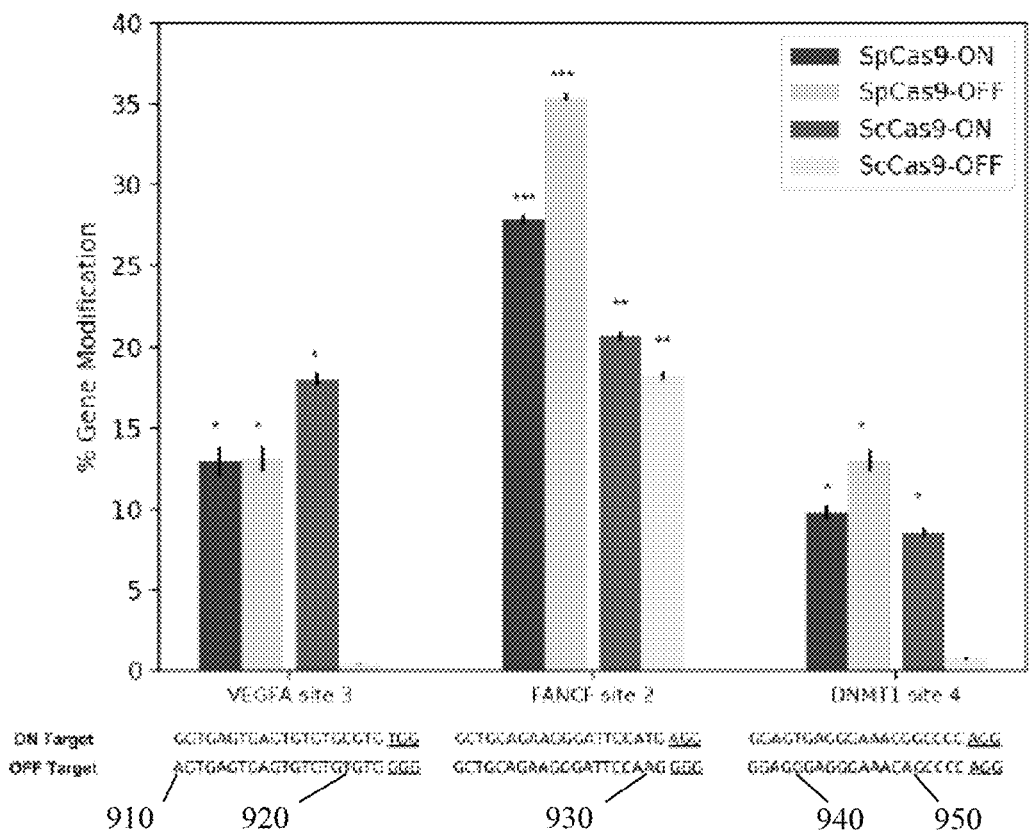

Consistent with previously-reported data [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)], SpCas9 demonstrated high off-to-on targeting on all three examined targets. ScCas9 demonstrated comparable on-target activities for the three targets, but exhibited negligible activity on the VEGFA site 3 and DNMT1 site 4 off-targets, and a nearly 1.5-fold decrease in off-to-on target ratio for FANCF site 2, suggesting improved accuracy over SpCas9 on overlapping 5'-NGG-3' targets. FIG. 9 is a graph of results from quantitative analysis of T7E1 products for indicated genomic on- and off-target editing. All samples were performed in duplicates and quantified modification values were averaged. Standard deviation was used to calculate error bars and statistical significance analysis was conducted using a two-tailed Student's t-test as compared to each negative control. Mismatched positions 910, 920, 930, 940, 950 within the spacer sequence are highlighted.

To examine ScCas9's accuracy across its wider PAM targeting range, a mismatch tolerance assay [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)] was utilized on target sequences with 5'-NAG-3', 5'-NCG-3', 5'-NGG-3', and 5'-NTG-3' PAMs. sgRNAs containing both single and adjacent double mismatches at every other base along each of the four on-target crRNA sequences were generated, and subsequently the genome modification efficiencies were measured for these mismatched sgRNAs. The results demonstrate that ScCas9 generally tolerates single mismatches better than double mismatches for each analyzed spacer position, and is similarly less likely to tolerate mismatches within the seed region of the crRNA, though with greater sensitivity than SpCas9, as shown in FIG. 10.

Figure 10:
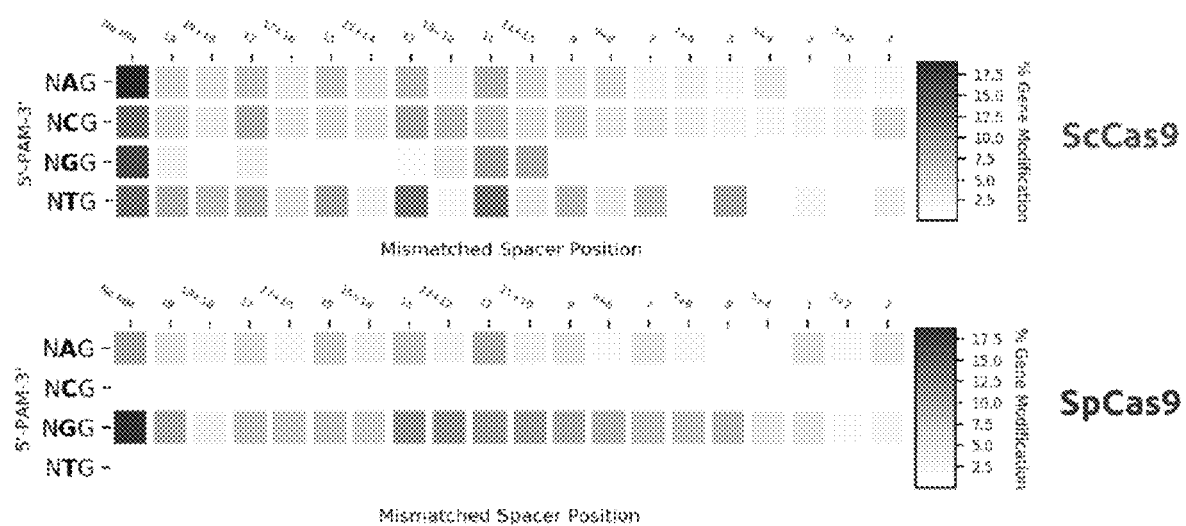

FIG. 10 is an efficiency heatmap of the mismatch tolerance assay. Quantified modification efficiencies, as assessed by the T7E1 assay, are exhibited for each labeled single or double mismatch in the sgRNA sequence for each indicated PAM. Across all of the four PAM targets, ScCas9 does tolerate mismatches within the middle of the crRNA sequence, with highest efficiencies reported for the 5'-NTG-3' target. SpCas9 expectedly demonstrates negligible genome modification activity on the 5'-NCG-3' and 5'-NTG-3' targets, but weakly tolerates single and double mismatches across the entire crRNA sequence, with reduced tolerance in the seed region, for the standard 5'-NGG-3' target, corroborating previous mismatch tolerance studies [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)]. Finally, ScCas9 exhibits a similar mismatch tolerance profile to SpCas9 on the 5'-NAG-3' target, albeit with a higher reported on-target efficiency.

ScCas9 Genome Editing Capabilities were evaluated for the ability to modify a variety of gene targets for a handful of different PAM sequences was evaluated. sgRNAs to 24 targets within 9 endogenous genes in HEK293T cells were constructed, and on-target gene modification was evaluated utilizing the T7E1 assay. The results demonstrate that ScCas9 maintains comparable efficiencies to that of SpCas9 on 5'-NGG-3' sequences, as well as on selected 5'-NNG-3' PAM targets, supporting the previous findings (FIG. 7).

Figure 11:
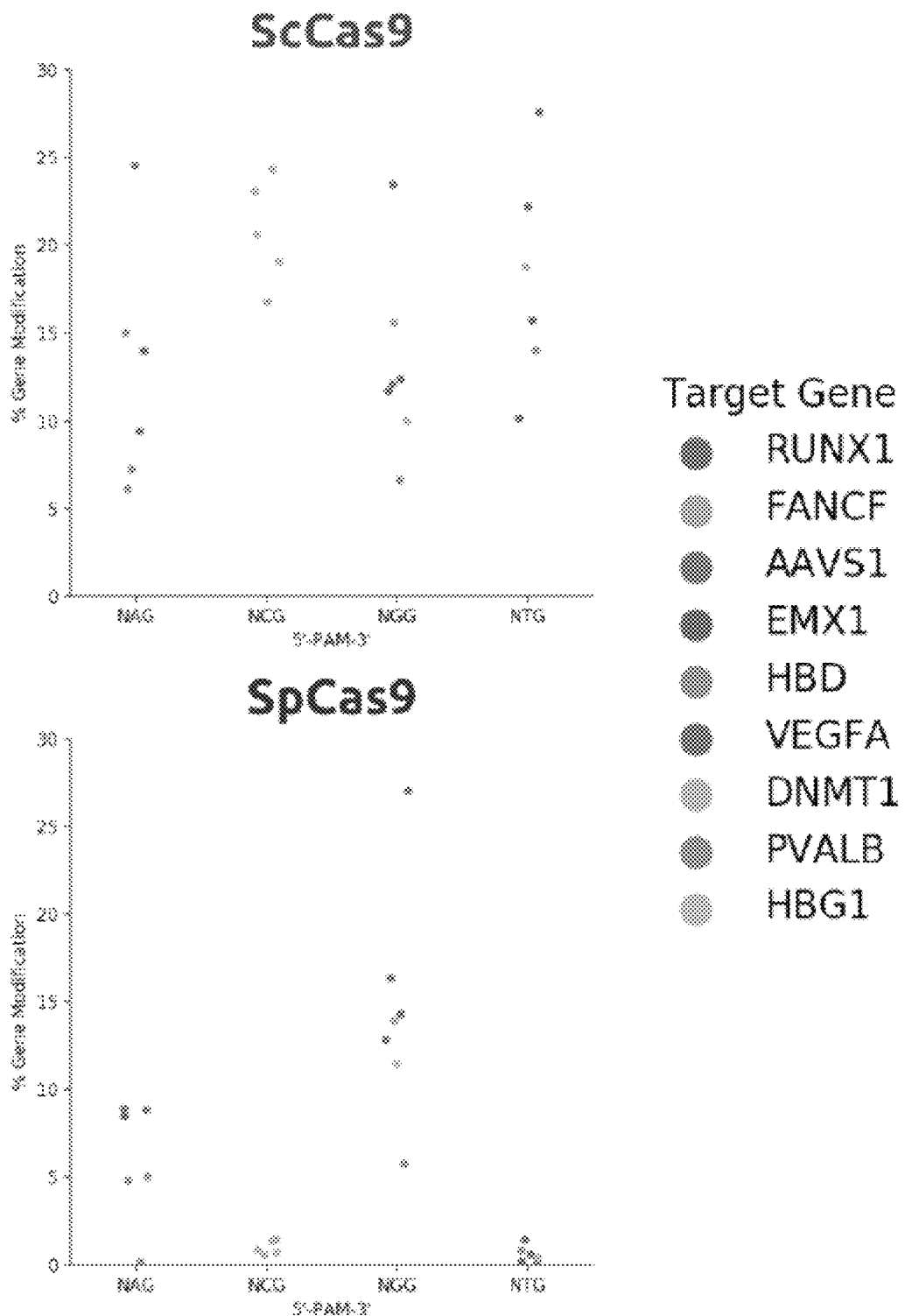

FIG. 11 is a dot plot of on-target modification percentages at various gene targets for indicated PAM as assessed by the T7E1 assay. Duplicate modification percentages were averaged. SpCas9 expectedly performs efficiently on 5'-NGG-3' and weakly on 5'-NAG-3' tar-gets, but demonstrates negligible editing capabilities on 5'-NCG-3' and 5'-NTG-3' PAM sequences, as previously demonstrated. Notably, ScCas9 performed less effectively on selected target sequences in the Hemoglobin subunit delta (HBD) gene, while demonstrating higher efficiencies on 5'-NNG-3' sequences in VEGFA and DNMT1, for example. Such variation in efficiency within each PAM group and across different genes indicates that proper target selection within specified genomic regions is critical for successful ScCas9-mediated gene modification.

The efficacy of ScCas9 integrated within the BE3 [A. C. Komor, Y. B. Kim, M. S. Packer, J. A. Zuris, D. R. Liu, "Programmable editing of a target base in genomic DNA without double-stranded DNA cleavage", Nature 533, 420-424 (2016)] and ABE(7.10) base editing architectures on endogenous genomic loci was subsequently measured. To evaluate the efficiency of base editing activities, a simple, easy-to-use Python program, termed the Base Editing Evaluation Program (BEEP), was developed, which takes as input both a negative control ab1 Sanger sequencing file and the edited sample ab1 file and outputs the efficiency of an indicated base conversion at a specific position (read 5' to 3') along the target sequence.

Figure 12:
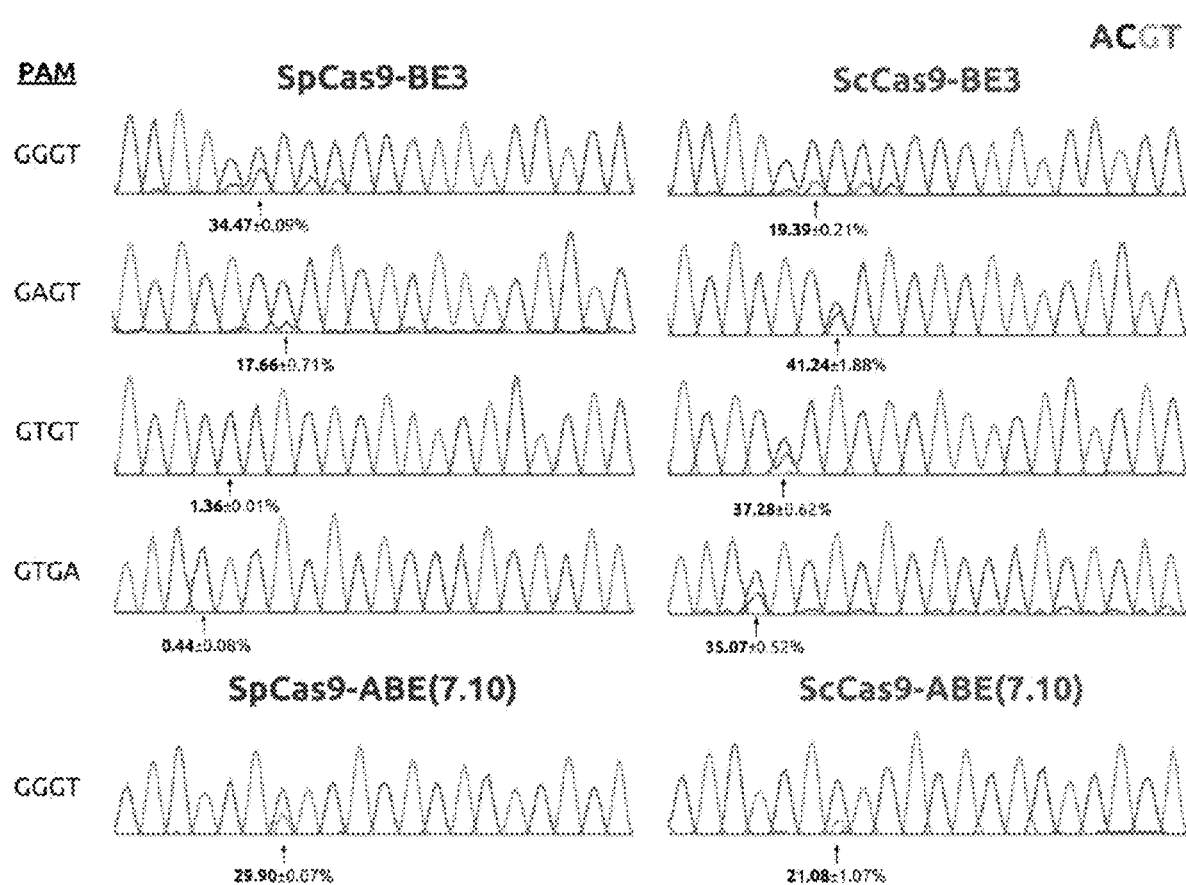

BEEP analysis on ab1 files, following transfection of ScCas9 base editors, genomic amplification, and subsequent Sanger sequencing, demonstrates that ScCas9 is capable of mediating C→T and A→G base conversion at both overlapping 5'-NGG-3' and nonoverlapping 5'-NNG-3' PAM sequences, as shown in FIG. 12, which depicts genomic base editing characterization. For each indicated PAM, a representative Sanger sequencing chromatogram is shown, demonstrating the most efficiently edited base in the target sequence. Percent edited values, as quantified by BEEP in comparison to an unedited negative control, were averaged and standard deviation was subsequently calculated. While ScCas9 base editors perform efficiently on the non-5'-NGG-3' targets, as compared to SpCas9 (FIGS. 8 and 12), ScCas9 is less effective at editing 5'-NGG-3' genomic targets than SpCas9 for both architectures, indicating that further development is necessary for broad usage of ScCas9 base editors.

Figure 13:
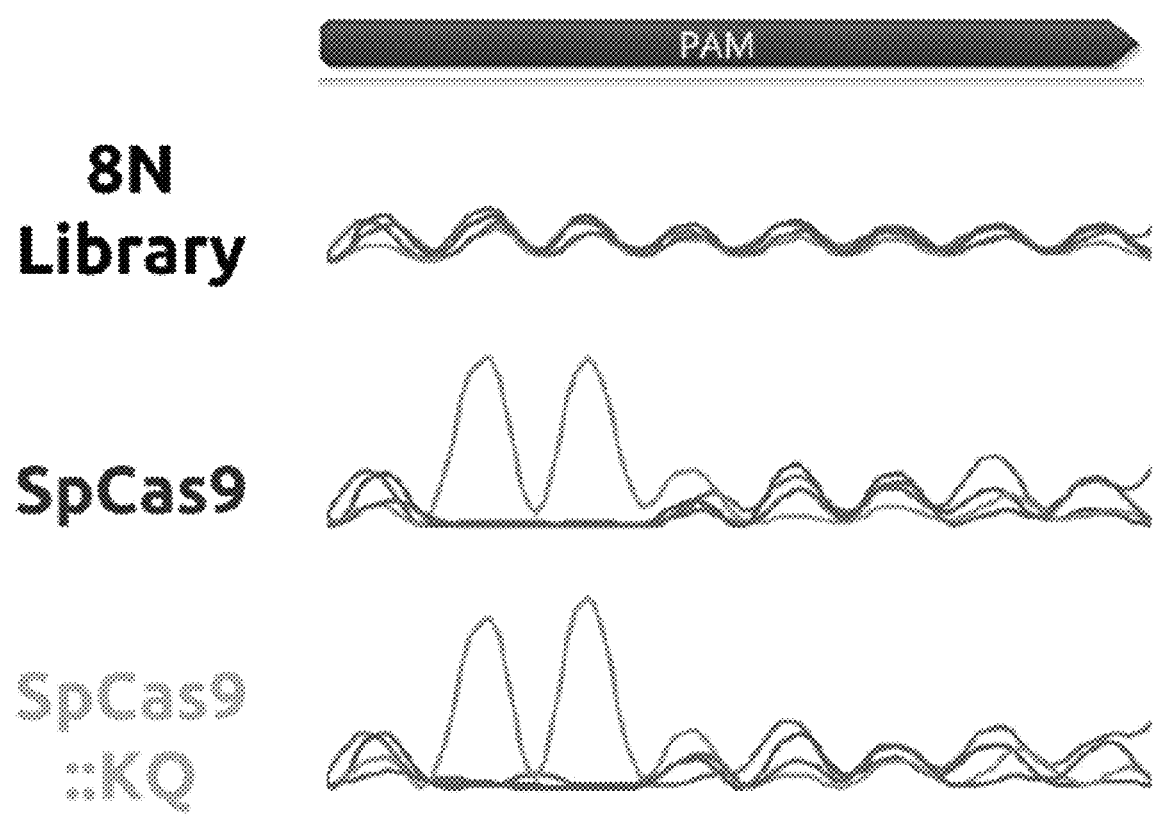
Figure 14:
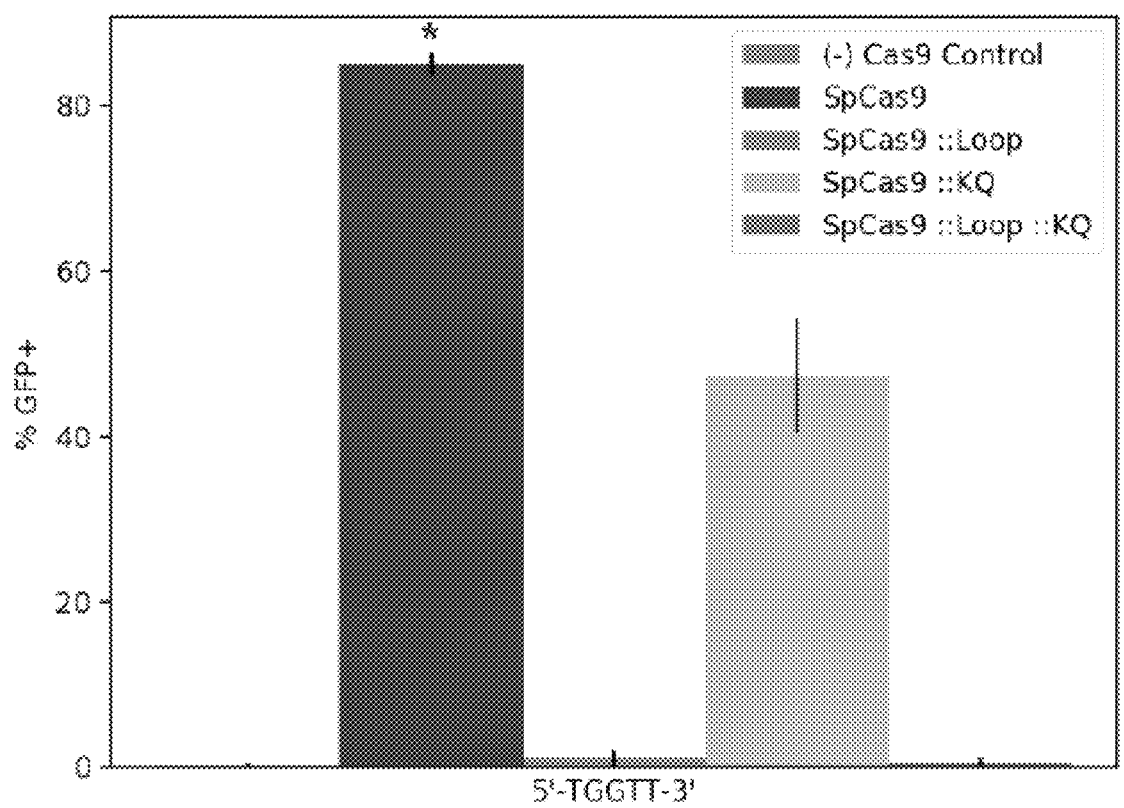

Investigation of Sequence Conservation between *S. canis* and other *Streptococcus* Cas9 orthologs To further investigate the distinguishing motif insertions in ScCas9, the loop (SpCas9::Loop), the KQ motif (SpCas9::KQ), or both (SpCas9::Loop::KQ) were inserted into the Sp-Cas9 ORF and binding on the 8N library was analyzed using PAM-SCANR. Of these variants, only SpCas9::KQ showed target binding affinity in the PAM-SCANR assay. Sequencing on enriched GFP-expressing cells demonstrated an unaffected preference for 5'-NGG-3'. FACS analysis on a fixed 5'-TGG-3' PAM confirmed these binding profiles, with SpCas9::KQ yielding half the fraction of GFP-positive cells compared to SpCas9. This data, in conjunction with the binding profiles of ScCas9 variants, suggests that while these insertions within ScCas9 do distinguish its PAM preference from SpCas9, other sequence features of ScCas9 also contribute to its divergence. FIG. 13 depicts PAM binding enrichment on a 5'-NNNNNNNN-3' PAM library of ScCas9-like SpCas9 variants. The PAM-SCANR screen (23) was applied to variants of SpCas9 containing either the loop or KQ insertions, or both. SpCas9::Loop and SpCas9::Loop::KQ failed to demonstrate PAM binding and thus GFP expression. FIG. 14 illustrates FACS analysis of binding at an 5'-NGG-3' PAM. All samples were performed in duplicates and averaged. Standard deviation was used to calculate error bars.

*S. canis* has been reported to infect dogs, cats, cows, and humans, and has been im-plicated as an adjacent evolutionary neighbor of *S. pyogenes*, as evidenced by various phylogenetic analyses [T. Lef ebure, V. P. Richards, P. Lang, P. Pavinski-Bitar, M. J. Stanhope, "Gene Repertoire Evolution of *Streptococcus pyogenes* Inferred from Phylogenomic Analysis with *Streptococcus canis* and *Streptococcus dysgalactiae*", PLOS ONE 7, e37607 (2012); 32. V. P. Richards, R. N. Zadoks, P. D. Pavinski Bitar, T. Lefbure, P. Lang, et al., "Genome characterization and population genetic structure of the zoonotic pathogen, *Streptococcus canis*", BMC Microbiol. 12, 293 (2012); V. P. Richards, S. R. Palmer, P. D. Pavinski Bitar, X. Qin, G. M. Weinstock, et al., "Phylogenomics and the Dynamic Genome Evolution of the Genus *Streptococcus*", Genome Biol. Evol. 6, 741-753 (2014)]. In addition to sharing common hosts, *S. canis* CRISPR spacers that map to phage lysogens in *S. pyogenes* genomes were identified, which suggests they are overlapping viral hosts as well. This close evolutionary relationship has manifested itself in the sequence homology of ScCas9 and SpCas9, amongst other orthologous genes, predicted to be a result of lateral gene transfer (LGT). Nonetheless, from the alignment of SpCas9 and ScCas9, the first 1240 positions score with 93.5% similarity and the last 144 positions score with 52.8%. To account for the exceptional divergence in the PAM-interacting domain (PID) at the C-terminus of ScCas9 as well as the positive-charged inserted loop, focus was placed on alignment of the distinguishing sequences of ScCas9 to other *Streptococcus* Cas9 orthologs. Notably, the loop motif is present in certain orthologs, such as those from *S. gordonii*, *S. anginosus*, and *S. intermedius*, while the ScCas9 PID is mostly composed of disjoint sequences from other orthologs, such as those from *S. phocae*, *S. varani*, and *S. equinis*. Additional LGT events between these orthologs, as opposed to isolated divergence, more likely explain the differences between ScCas9 and SpCas9. The demonstration that two insertion motifs in ScCas9 alter PAM preferences, yet do not abolish PAM binding when removed, suggests other functional evolutionary intermediates in the formation of effective PAM preferences.

Genus-Wide Prediction of Divergent *Streptococcus* Cas9 PAMs

Demonstrations of efficient genome editing by Cas9 nucleases with distinct PAM specificity from several *Streptococcus* species, including *S. canis*, motivated development of a bioinformatics pipeline for discovering additional Cas9 proteins with novel PAM requirements in the *Streptococcus* genus. This method was termed the Search for PAMs by ALignment Of Targets (SPAMALOT). Briefly, a 20 nt portion of spacers flanked by known *Streptococcus* repeat sequences was mapped to candidate protospacers that align with no more than two mismatches in phages associated with the genus [S. A. Shmakov, V. Sitnik, K. S. Makarova, Y. I. Wolf, K. V. Severinov, et al., "The CRISPR Spacer Space Is Dominated by Sequences from Species-Specific Mobilomes", mBio 8, e01397-17 (2017)]. 12 nt protospacer3'-adjacent sequences from each alignment were grouped by genome and CRISPR repeat, and then group WebLogos were generated to compute presumed PAM features.

Figure 15:
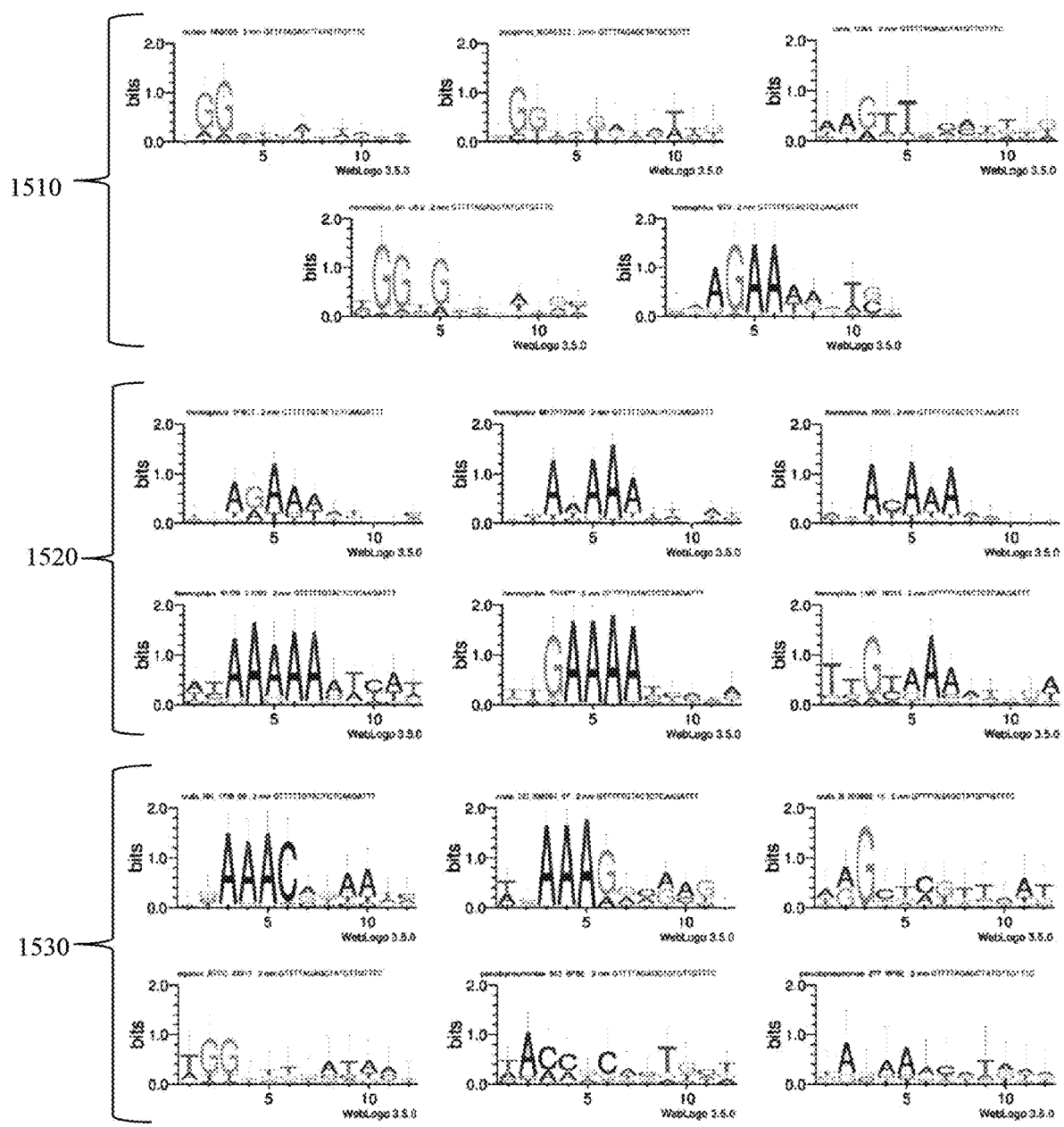
FIG. 15 depicts SPAMALOT PAM Predictions for Streptococcus Cas9 Orthologs.

FIG. 15 depicts SPAMALOT PAM Predictions for *Streptococcus* Cas9 Orthologs. Spacer sequences found within the Type II CRISPR cassettes associated with Cas9 ORFs from specified *Streptococcus* genomes were aligned to *Streptococcus* phage genomes to generate spacer-protospacer mappings. WebLogos, labeled with the relevant species, genome, and CRISPR repeat, were generated for sequences found at the 3' end of candidate protospacer targets with no more than two mismatches (2 mm). Shown in FIG. 15 are PAM predictions for experimentally validated Cas9 PAM sequences 1510 in previous studies, novel PAM predictions of alternate *S. thermophilus* Cas9 orthologs 1520 with putative divergent specificities, and novel PAM predictions of uncharacterized *Streptococcus* orthologs 1530 with distinct specificities.

FIG. 15 1510 shows that resulting WebLogos accurately reflect the known PAM specificities of Cas9 from *S. canis* (this work), *S. pyogenes*, *S. thermophilus*, and *S. mutans* [S. H. Sternberg, S. Redding, M. Jinek, E. C. Greene, J. A. Doudna, "DNA interrogation by the CRISPR RNA-guided endonuclease Cas9", Nature 507, 62-67 (2014); M. Muller, C. M. Lee, G. Gasiunas, T. H. Davis, T. J. Cradick, et al., "*Streptococcus thermophilus* CRISPR-Cas9 Systems Enable Specific Editing of the Human Genome, Mol. Ther. 24, 636-644 (2016); I. Fonfara, A. L. Rhun, K. Chylinski, K. S. Makarova, A. L. Lcrivain, et al., "Phylogeny of Cas9 determines functional exchangeability of dual-RNA and Cas9 among orthologous type II CRISPR-Cas systems", Nucleic Acids Res. 42, 2577-2590 (2014)]. A notable diversity was identified in the WebLogo plots derived from various *S. thermophilus* cassettes with common repeat sequences 1520, each of which could originate from any other such *S. thermophilus* WebLogo upon subtle specificity changes that traverse intermediate WebLogos among them. A similar relationship was observed between two *S. oralis* WebLogos that also share this repeat, as well as unique putative PAM specificities associated with CRISPR cassettes containing *S. mutans*-like repeats from the *S. oralis, S. equinis*, and *S. pseudopneumoniae* genomes (FIG. 15 1530).

As the growth and development of CRISPR technologies continue, the range of targetable sequences remains limited by the requirement for a PAM sequence flanking a given target site. While significant discovery and engineering efforts have been undertaken to expand this range, there are still only a handful of CRISPR endonucleases with minimal specificity requirements. Here, an analogous platform for genome editing using the Cas9 from *Streptococcus canis*, a highly-similar SpCas9 ortholog with affinity to minimal 5'-NNG-3' PAM sequences has been developed.

Established PAM engineering methods, such as random mutagenesis and directed evolution, can only generate substitution mutations in protein coding sequences. In fact, another group utilized phage assisted continuous evolution (PACE) [K. M. Esvelt, J. C. Carlson, D. R. Liu, "A system for the continuous directed evolution of biomolecules", Nature 472, 499-503 (2011)] to evolve an SpCas9 variant, xCas9(3.7), with preference for various 5'-NG-3' PAM sequences [J. H. Hu, S. M. Miller, M. H. Geurts, W. Tang, L. Chen, et al., "Evolved Cas9 variants with broad PAM compatibility and high DNA specificity", Nature 556, 5763 (2018)]. An alternative approach consists of inserting or removing motifs with specific properties, which may provide a sequence search space that more common mutagenic techniques cannot directly access. Here, an evolutionary example of this method is demonstrated with ScCas9, whose sequence disparities with SpCas9 include two divergent motifs that contribute to its minimal PAM sequence. Engineered variants lacking these motifs exhibit more stringent PAM specificities in PAM determination assays, and the removal of both motifs reverts its PAM specificity back to a more 5'-NGG-3'-like preference. While minimal inconsistencies in PAM preference between the utilized assays may arise from PAM-dependent allosteric changes that drive DNA cleavage [C. Anders, K. Bargsten, M. Jinek, "Structural plasticity of PAM recognition by engi-neered variants of the RNA-guided endonuclease Cas9", Mol. Cell 61, 895-902 (2016)], the PAM flexibility of ScCas9, as compared to SpCas9, remains consistent in all tested contexts.

To date, there are limited open-source tools or platforms specifically for the prediction of PAM sequences, though prior studies have conducted internal bioinformatics-based characterizations prior to experimental validation. Here, SPAMALOT is established as an accessible resource that is shared with the community for application to CRISPR cassettes from other genera. Future development will include broadening the scope of candidate targets beyond genus-associated phage to capture additional sequences that could be beneficial targets, such as lysogens in species that host the same phage. It is hoped that this pipeline can be utilized to more efficiently validate and engineer PAM specificities that expand the targeting range of CRISPR, especially for strictly PAM-constrained technologies such as base editing and homology repair induction.

Because ScCas9 does not require any alterations to the sgRNA of SpCas9, and due to its significant sequence homology with SpCas9, identical modifications from previous studies [I. M. Slaymaker, L. Gao, B. Zetsche, D. A. Scott, W. X. Yan, et al., "Rationally engineered Cas9 Nucleases with improved specificity", Science 351, 84-88 (2016); B. P. Kleinstiver, V. Pattanayak, M. S. Prew, S. Q. Tsai, N. T. Nguyen, et al., "High-fidelity CRISPR-Cas9 nucleases with no detectable genome-wide off-target effects", Nature 529, 490-495 (2016); J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)] can be made to increase the accuracy and efficiency of the endonuclease and its variants, although it already demonstrates potential improved on-to-off activity as compared to the standard SpCas9 on 5'-NGG-3' targets. Additionally, while the PAM specificity of ScCas9 on multiple targets in a variety of genome editing contexts has been exhaustively evaluated, the possibility remains that there may exist untested 5'-NNG-3' genomic targets on which ScCas9 does not possess significant activity. Used together with SpCas9 and xCas9(3.7), however, ScCas9 expands the target range of currently-used Cas9 enzymes for genome editing purposes. With further development, this broadened *Streptococcus* Cas9 toolkit, containing both ScCas9 and additional, uncharacterized orthologs with expanded targeting range, will enhance the current set of CRISPR technologies.

Applications of engineered *Streptococcus canis* Cas9 variants on single base PAM targets.

Specifically, the claimed invention comprises use of either the ScCas9 endonuclease with a T1227K (ScCas9+) or the PAM-interacting domain of SpCas9-NG grafted onto the N-terminal domain of ScCas9 (ScCas9-NG), in complex with guide RNA to enable specific recognition and activity on a DNA target immediately upstream of either an 5'-NG-3' or 5'-NNG-3' PAM sequence, promoting improved flexibility in target selection.

To validate the predicted minimal G-rich PAM sequence of the described variants, a bacterial assay based upon lad promoter repression of GFP expression, employing a fully randomized 8-nucleotide library of PAM sequences upstream of lad, was utilized [Leenay, R. T. et al., "Identifying and visualizing functional PAM diversity across CRISPR-Cas systems", Mol. Cell 62, 137-147 (2016)]. The library-containing plasmids were co-electroporated with a gRNA plasmid and a nuclease-activity deficient SpMacCas9 (dSpMacCas9) plasmid, all expressing different antibiotic resistance cassettes (Kanamycin, Ampicillin, Chloramphenicol, respectively). Transformants were collected in 5 ml of triple antibiotic-containing Luria Broth (LB) media. Overnight cultures were diluted to an ABS600 of 0.01 and cultured to an OD600 of 0.2. Cultures were analyzed and sorted on a FACSAria machine (Becton Dickinson). Events were gated based on forward scatter and side scatter and fluorescence was measured in the FITC channel (488 nm laser for excitation, 530/30 filter for detection), with at least 30,000 gated events for data analysis. Sorted GFP-positive cells were grown to sufficient density, and plasmids from the pre-sorted and sorted populations were then isolated, and the region flanking the nucleotide library was PCR amplified and submitted for Sanger sequencing (Genewiz).

Figure 16:
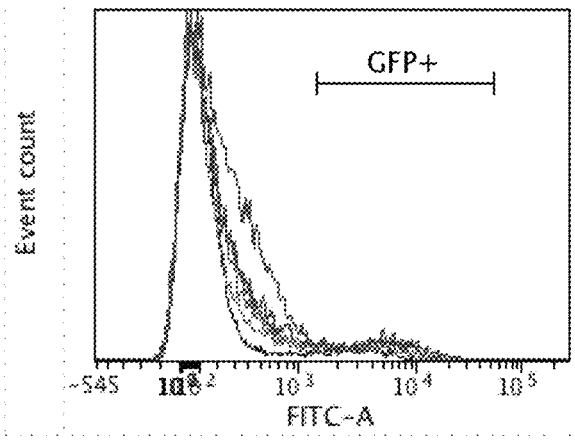
FIG. 16 illustrates results from histograms of the fluorescein isothiocyanate (FITC) channel, demonstrating a significant increase of GFP-positive cells for both ScCas9-NG as well as ScCas9+, as compared to SpCas9, ScCas9, and SpCas9-NG, according to an aspect of the invention.
Figure 17:
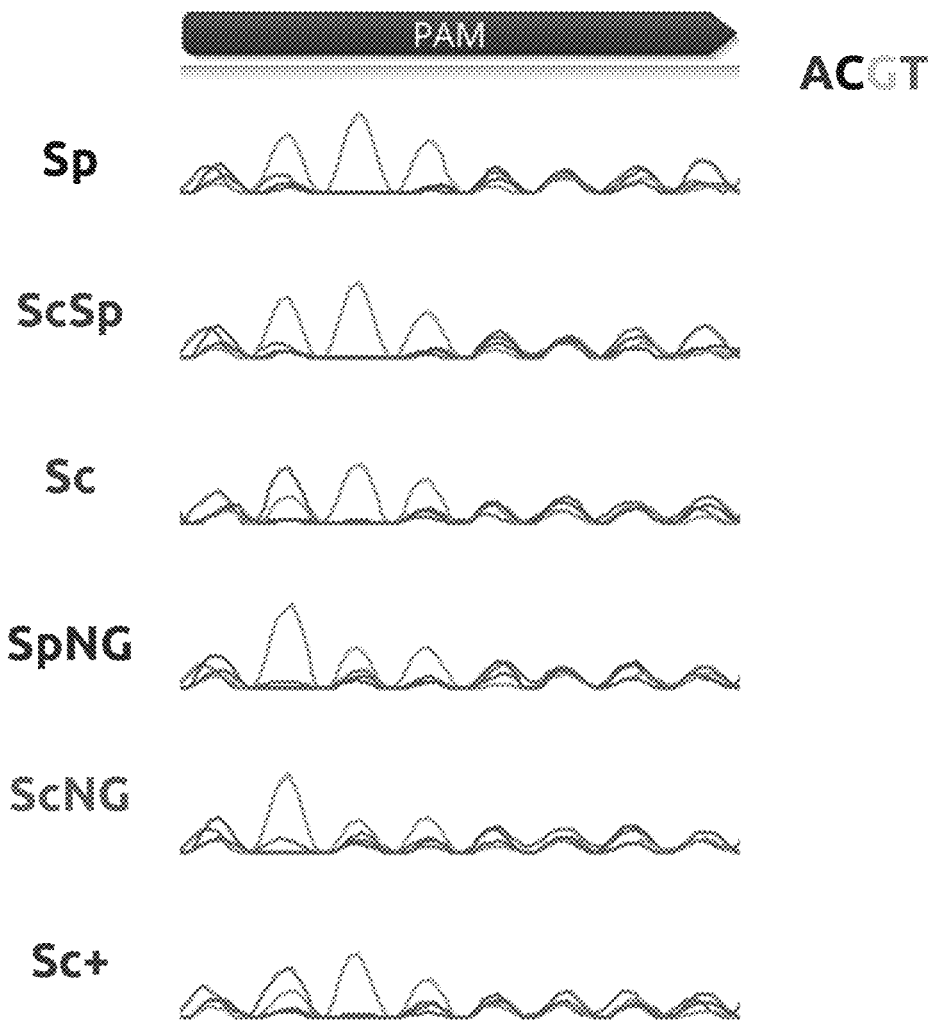
FIG. 17 depicts sequencing chromatograms demonstrating enrichment of G at position 2 for ScCas9-NG and at position 3 for ScCas9+, together with the histogram data, confirming the improved 5'-NG-3' specificity of ScCas9-NG and 5'-NNG-3' specificity of ScCas9+ in bacterial cells, according to an aspect of the invention.

Histograms of the fluorescein isothiocyanate (FITC) channel demonstrate a significant increase of GFP-positive cells for both ScCas9-NG as well as ScCas9+, as compared to SpCas9, ScCas9, and SpCas9-NG (FIG. 16). Additionally, the sequencing chromatograms demonstrate enrichment of G at position 2 for ScCas9-NG and at position 3 for ScCas9+, together with the histogram data, confirming the improved 5'-NG-3' specificity of ScCas9-NG and 5'-NNG-3' specificity of ScCas9+ in bacterial cells (FIG. 17).

In some implementations, the invention includes the application of ScCas9-NG and ScCas9+ as tools for genome engineering in human cells. Briefly, the coding sequence of the described Cas9 variants are transiently transfected, using standard lipofection reagents (e.g. Lipofectamine 2000), as plasmids under the control of an Elongation Factor 1-alpha (EF1-α) promoter in HEK293T cells along with guide RNA vectors under the control of a U6 promoter containing spacer sequences targeting various 5'-NG-3' and 5'-NNG-3' PAM sequences at the standard VEGFA locus. After 5 days post transfection, individual cells are harvested for genomic extraction to allow for an approximately one kilobase (kb) window around the target to be amplified via polymerase chain reaction (PCR). Indel formation can be further verified on Sanger sequencing results utilizing the TIDE algorithm or ICE (Synthego). The invention further includes utilizing the described variants for applications such as, but not limited to, specific base conversions and gene regulation applications, such as transcriptional activation and repression.

For in vitro and in vivo applications, the invention is compatible with additional delivery methods used for other CRISPR-Cas9 systems including, but not limited to, electroporation, viral infection, and nanoparticle injection. Embodiments can co-deliver the invention as a coding nucleic acid or protein, along with a gRNA. Components can also be stably expressed in cells.

Engineering and PAM Determination of ScCas9++ Variant

SpCas9-NG and xCas9-3.7 both harbor various substitutions in their open reading frames (ORFs) that allow reduced specificity from the canonical 5'-NGG-3' to the more minimal 5'-NGN-3' PAM. Specifically, positions 1218-1219 for both enzymes have been shown to be the most consequential in terms of PAM recognition [H. Nishimasu, X. Shi, S. Ishiguro, L. Gao, S. Hirano, et al., "Engineered CRISPR-Cas9 nuclease with expanded targeting space", Science 361, 1259-1262 (2018); M. Guo, K. Ren, Y. Zhu, Z. Tang, Y. Wang, et al., "Structural insights into a high fidelity variant of SpCas9", Cell Research 29, 183192 (2019)]. To engineer ScCas9 to possess improved PAM targeting capabilities, global pairwise alignments were performed using the BLOSUM62 scoring matrix [S. Henikoff, J. G. Henikoff, "Amino acid substitution matrices from protein blocks", Proc. Natl. Acad. Sci. 89, 10915-10919 (1992] of various Streptococcus Cas9 orthologs to SpCas9, xCas9-3.7, and SpCas9-NG at these critical residues. The sequence alignment isolated a positive-charged lysine residue, derived from the S. gordonii Cas9 ORF. Substituting positive-charged residues into the PAM-interacting domain (PID) of Cas enzymes has been suggested to allow for the formation of novel PAM-proximal DNA contacts [B. P. Kleinstiver, A. A. Sousa, R. T. Walton, Y. E. Tak, J. T. Hsu, et al., "Engineered CRISPR-Cas12a variants with increased activities and improved targeting ranges for gene, epigenetic and base editing", Nat. Biotechnol. 37, 276-282 (2019)]. Motivated by this finding, the corresponding T1227K mutation was substituted into the ORF of ScCas9, generating ScCas9+(Sc+).

One of the defining characteristics of ScCas9's PAM flexibility is its employment of a positive-charged loop, in positions 367 to 376 of its ORF, which does not exist in SpCas9 or its engineered variants [P. Chatterjee, N. Jakimo, J. M. Jacobson, "Minimal PAM specificity of a highly similar SpCas9 ortholog", Science Advances 4:10, eaau0766 (2018)]. The obtained sequence alignments identified a divergent insertion from S. anginosus, which not only maintains the positive charge of the ScCas9 loop by compensating an extra lysine residue for a histidine, but also possesses an "SG" motif, a flexible sequence of residues used for linker design in protein engineering [X. Chen, J. Zaro, W. C. Shen, "Fusion Protein Linkers: Property, Design and Functionality", Adv. Drug. Deliv. Rev. 65, 13571369 (2012)]. It was hypothesized that this novel loop may improve the targeting capabilities and efficiency of ScCas9 by allowing for more flexible protein-phosphate backbone contacts with the PAM sequence. Thus, the loop sequence from S. anginosus was substituted into the Sc+ ORF to generate ScCas9++(Sc++), as illustrated in FIG. 18.

Figure 18:
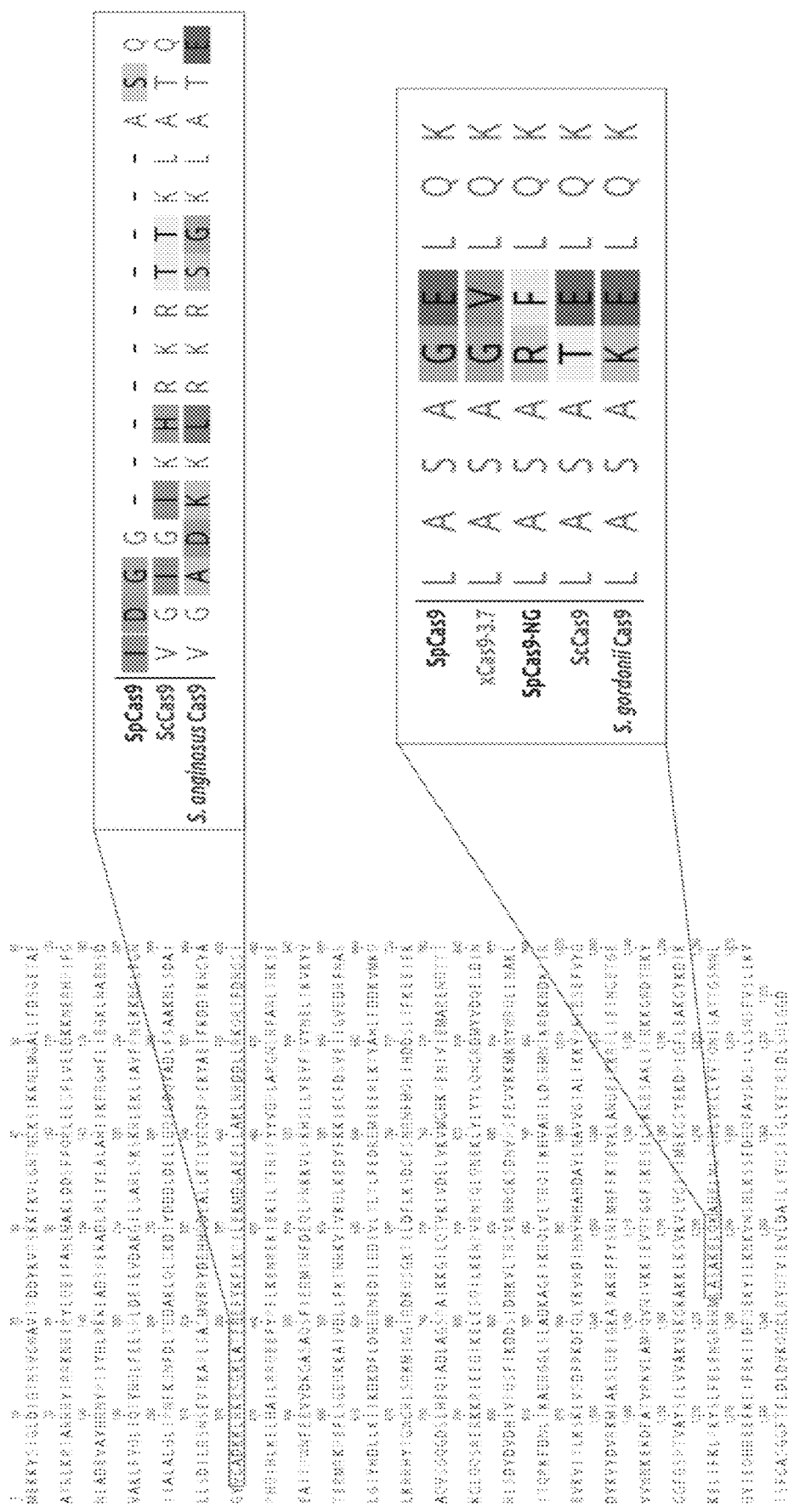

FIG. 18 depicts the amino acid sequence of ScCas9++, showing the T1227K mutation derived from Streptococcus gordonii and the novel loop structure from Streptococcus anginosus that harbors an additional lysine residue and a flexible "SG" motif, according to an aspect of the invention. SpCas9, SpCas9-NG, xCas9-3.7, and ScCas9 were aligned with various Streptococcus Cas9 orthologs, employing the BLOSUM62 scoring matrix, to identify the T1227K mutation derived from Streptococcus gordonii. Sequence alignment of ScCas9 with various Streptococcus Cas9 orthologs further isolated the novel loop structure from Streptococcus anginosus.

Determination of PAM Sequences Recognized by Engineered ScCas9 Variants

To comprehensively profile the PAM specificity of Sc+ and Sc++, in comparison to SpCas9, xCas9-3.7, and SpCas9-NG, as well as the wild-type ScCas9, a previously-developed positive selection bacterial screen based on green fluorescent protein (GFP) expression conditioned on PAM binding, termed PAM-SCANR [R. T. Leenay, K. R. Maksimchuk, R. A. Slotkowski, R. N. Agrawal, A. A. Gomaa, et al., "Identifying and Visualizing Functional PAM Diversity across CRISPR-Cas Systems", Mol. Cell 62, 137-147 (2016)], was utilized. Following transformation of the PAM-SCANR plasmid, harboring a randomized 5'-NNNNNNNN-3' (8N) PAM library, an sgRNA plasmid targeting the fixed PAM-SCANR protospacer, and a corresponding dCas9 plasmid, FACS analysis was conducted to first determine the percent of GFP-positive cells in each population, a relative proxy for the percent of total PAM sequences being bound.

Figure 19A:
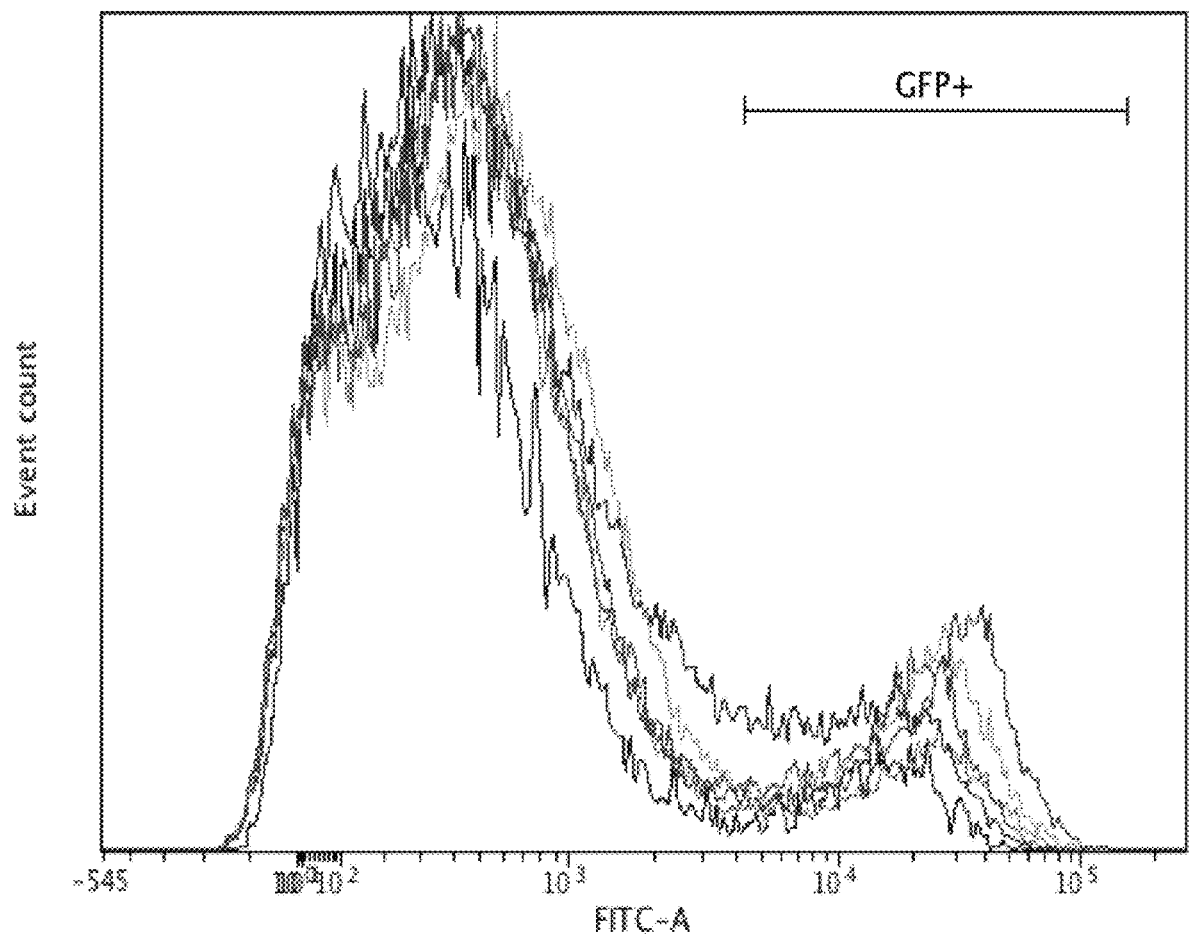
FIGS. 19A-B graphically illustrate PAM binding analysis of single G PAM Cas9 variants on a 5'-NNNNNNNN-3' (8N) PAM library.
Figure 19B:
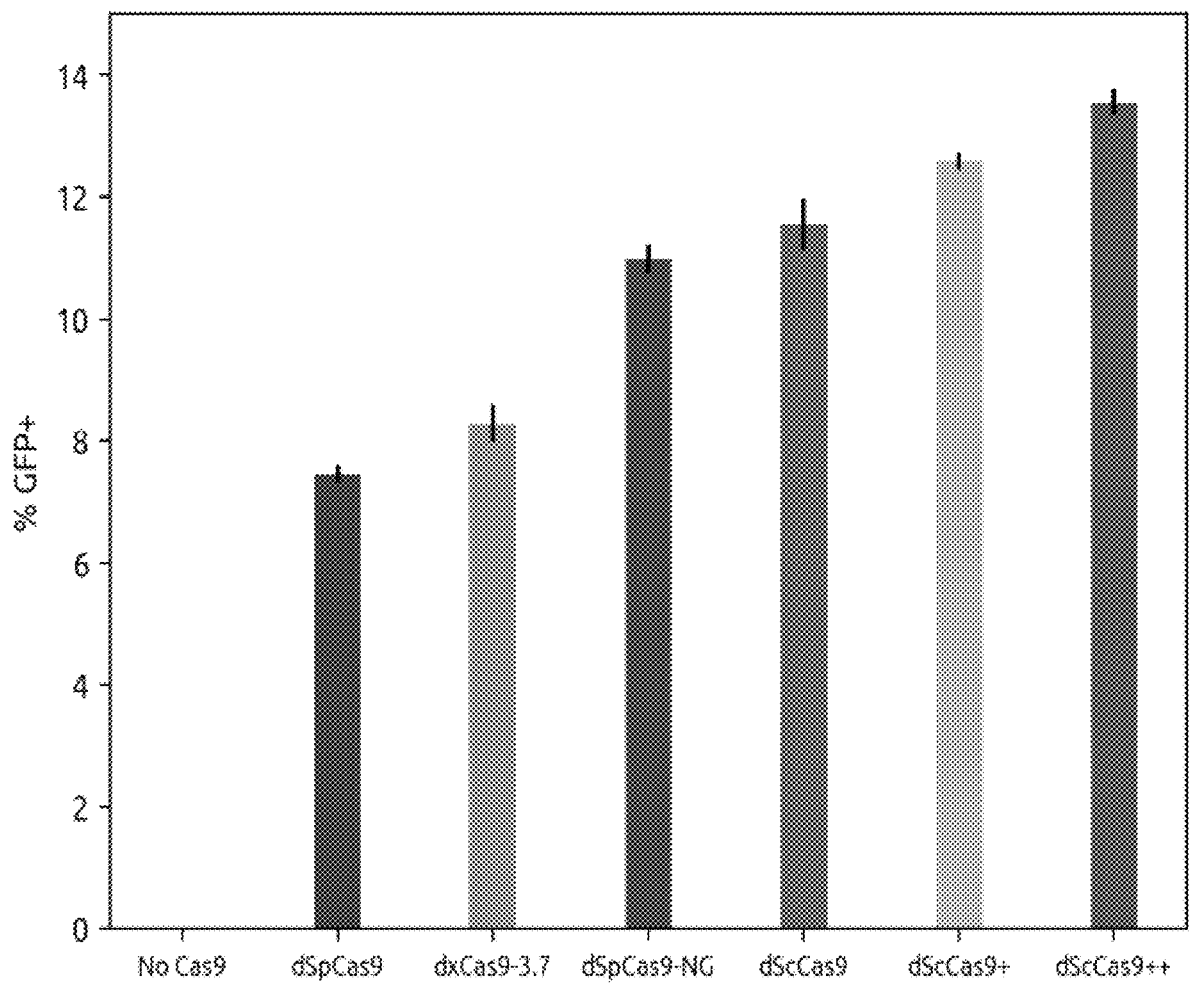

The results demonstrated that both dSc+ and dSc++ bind to a greater percentage of PAM sequences, and dSc++ exhibits a shifted GFP-positive population, suggesting stronger binding capabilities and improved efficiency, as seen in FIGS. 19A and 19B, which present results from PAM binding analysis of single G PAM Cas9 variants on a 5'-NNNNNNNN-3' (8N) PAM library. Each dCas9 plasmid was electroporated in duplicates, subjected to FACS analysis, and gated for GFP expression. Subsequently, percentages of GFP-positive cells were averaged. Standard deviation was used to calculate error bars.

Figure 20:
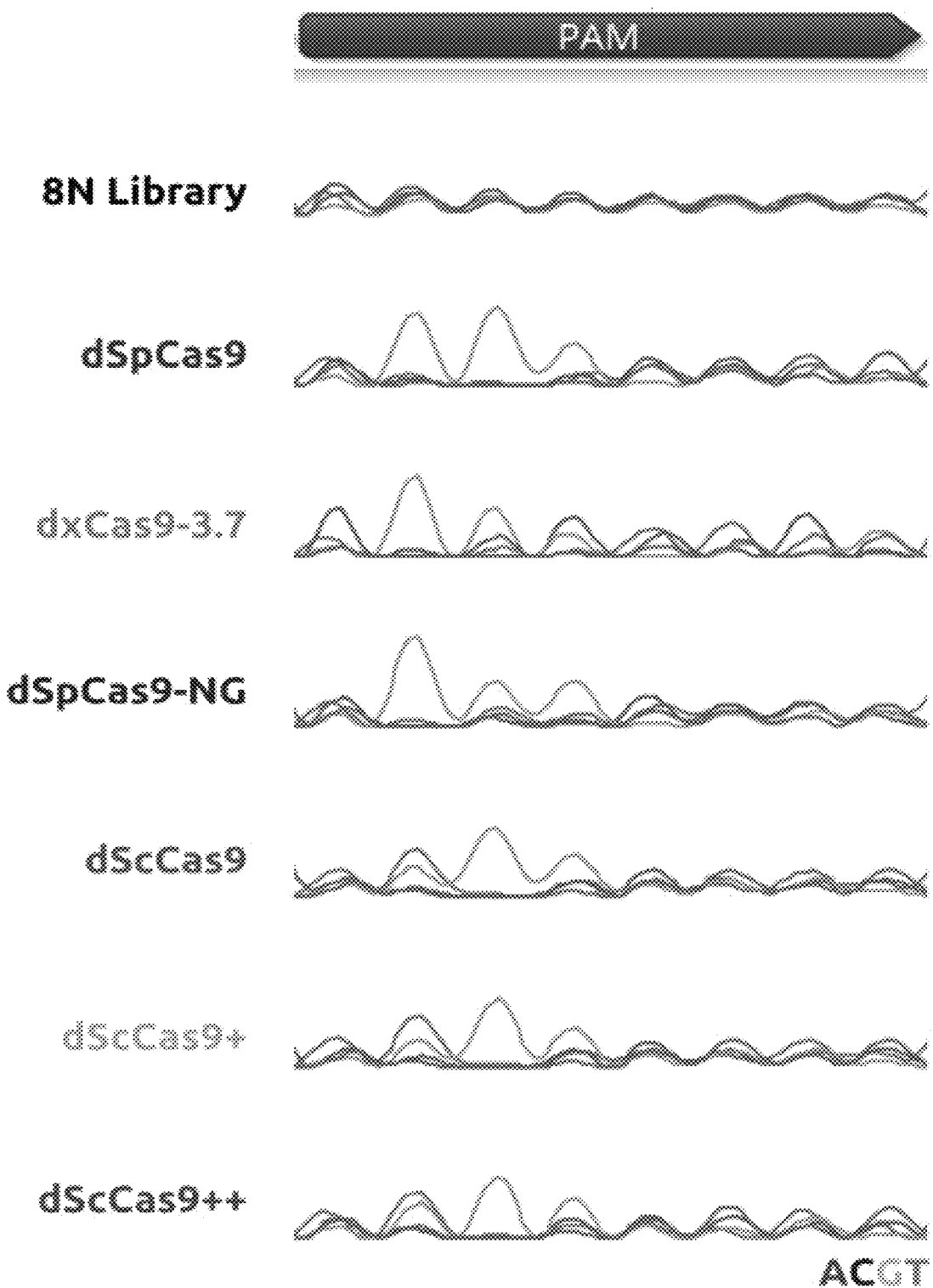

Plasmid DNA from FACS-sorted GFP-positive cells and presorted cells were then extracted and amplified, and enriched PAM sequences were identified by Sanger sequencing, and visualized utilizing DNA chromatograms. Sequencing results indicate that the ScCas9 variants possess improved PAM specificity, as compared to xCas9-3.7, which demonstrates notable dependence on bases in downstream positions, and SpCas9-NG, which may require additional G nucleotides in positions 3 or 4 for efficient binding. FIG. 20 depicts PAM profiles as represented by DNA chromatograms via amplification of PAM region following plasmid extraction of GFP-positive *E. coli* cells and subsequent Sanger sequencing. While exhibiting similar specificity to ScCas9 and Sc+, Sc++ comparatively enjoys greater independence at position 4 in the PAM sequence. Taken together, these results suggest that Sc+ and Sc++ possess broader targeting capabilities and, potentially, enhanced efficiency for genome editing applications, thus prompting their characterization in human cells.

Genome Editing Capability of Engineered ScCas9 Variants

The PAM specificities and nucleolytic capabilities of Sc+ and Sc++ were compared to SpCas9, xCas9-3.7, SpCas9-NG, and ScCas9 by transfecting HEK293T cells with plasmids expressing each variant individually alongside one of 16 sgRNAs, together directed to four genomic loci with diverse PAM sequences, collectively representing every base at each position in the PAM window (Table 2). The sgRNA sequences were shifted by one base for xCas9-3.7 and SpCas9-NG to account for their reported 5'-NGN-3' PAM preferences, so as to equivalently compare these enzymes to ScCas9 variants with 5'-NNG-3' specificities.

Table 2 summarizes the relevant sequence information for genome editing in human cells. Spacer and PAM sequences indicated are for use with ScCas9 variants and the standard SpCas9. All sequences for xCas9-3.7 and SpCas9-NG are shifted one base in the 3' direction for equivalent comparison purposes, due to their reported 5'-NGN-3' PAM sequences.

TABLE 2

| 5'-Spacer-3' | 5'-PAM-3' | Gene | Editing Context |
|---|---|---|---|
| GGAGGGTGGCGAGAGGGGCC [SEQ ID No: 7] | GAGATTG | PVALB | Nuclease |
| TCTGACAATAGTCCTGTCTG [SEQ ID No: 8] | GTGCATT | PVALB | Nuclease |
| AAATGAATGAATGAGCAGAT [SEQ ID No: 9] | GAGTGAA | PVALB | Nuclease |
| CCAGAAGAATGGTGTCATTA [SEQ ID No: 10] | GAGGGCC | PVALB | Nuclease |
| ATTTCATTACAGGCAAAGCT [SEQ ID No: 11] | GAGCAAA | RUNX1 | Nuclease/Base Editing |
| GAAAATGCACCCTCTTCTGA [SEQ ID No: 12] | AGGCGGG | RUNX1 | Nuclease |
| GCTGAAACAGTGACCTGTCT [SEQ ID No: 13] | TGGTTTT | RUNX1 | Nuclease |
| AAACACCATGTACCACACAT [SEQ ID No: 14] | GTGAACG | DNMT1 | Nuclease |
| GGATTCCTGGTGCCAGAAAC [SEQ ID No: 15] | AGGGGTG | DNMT1 | Nuclease |
| GTTAACAGCTGACCCAATAA [SEQ ID No: 16] | GTGGCAG | DNMT1 | Nuclease |
| ATGTGAACGGACAGATTGAC [SEQ ID No: 17] | ATGTTAA | DNMT1 | Nuclease |
| GGTCTAGAACCCTCTGGGGA [SEQ ID No: 18] | CCGTTTG | DNMT1 | Nuclease/Mismatch |
| GCACCAGCGGACCCACACGG [SEQ ID No: 19] | GCGAGAA | ZSCAN2 | Nuclease |
| CATTCTGGTCATGCACCAGA [SEQ ID No: 20] | GAGCCCA | ZSCAN2 | Nuclease |
| ACAGGGGAGAAACCCTACGA [SEQ ID No: 21] | GTGCCTG | ZSCAN2 | Nuclease |
| GATGTGTGATAAAGTTAGAG [SEQ ID No: 22] | CTGTTGC | ZSCAN2 | Nuclease |
| GCCAGTCTCGATCCGCCCCG [SEQ ID No: 23] | TCGTTCC | AAVS2 | Base Editing |
| GCGGATCGAGACTGGCAACG [SEQ ID No: 24] | GGGAAGG | AAVS2 | Base Editing |
| GCTCGGCCACCACAGGGAAG [SEQ ID No: 25] | CTGGGTG | VEGF | Base Editing |

After 5 days post-transfection, indel formation was quantified from Sanger sequencing ab1 files using the TIDE algorithm [E. K. Brinkman, T. Chen, M. Amendola, B. V. Steensel, "Easy quantitative assessment of genome editing by sequence trace decomposition", Nucleic Acids Res. 42, e168 (2014)] following PCR amplification of the target genomic region. The results demonstrate that Sc+ and Sc++ can effectively edit across the various genomic loci, and demonstrate improved indel formation percentages for a majority of the targets tested. SpCas9, xCas9-3.7, and SpCas9-NG all edit on "GG" PAM targets, and maintain activity on various 5'-AGN-3' PAM sequences. While xCas9-3.7 and SpCas9-NG additionally edit few sites that harbor 5'-CGN-3' and 5'-TGN-3' sequences, they performed poorly on all tested 5'-NGC-3' PAM targets, consistent with previously reported data [J. H. Hu, S. M. Miller, M. H. Geurts, W. Tang, L. Chen, et al., "Evolved Cas9 variants with broad PAM compatibility and high DNA specificity", Nature 556, 5763 (2018); H. Nishimasu, X. Shi, S. Ishiguro, L. Gao, S. Hirano, et al., "Engineered CRISPR-Cas9 nuclease with expanded targeting space", Science 361, 1259-1262 (2018); K. Hua, X. Tao, P. Han, R. Wang, J. K. Zhu, "Genome engineering in rice using Cas9 variants that recognize NG PAM sequences", Mol. Plant (2019); Z. Zhong, S. Stretenovic, Q. Ren, L. Yang, Y. Bao, et al. "Improving plant genome editing with high-fidelity xCas9 and non-canonical PAM-targeting Cas9-NG", Mol. Plant (2019); M. Guo, K. Ren, Y. Zhu, Z. Tang, Y. Wang, et al., "Structural insights into a high fidelity variant of SpCas9", Cell Research 29, 183192 (2019)].

Figure 21:
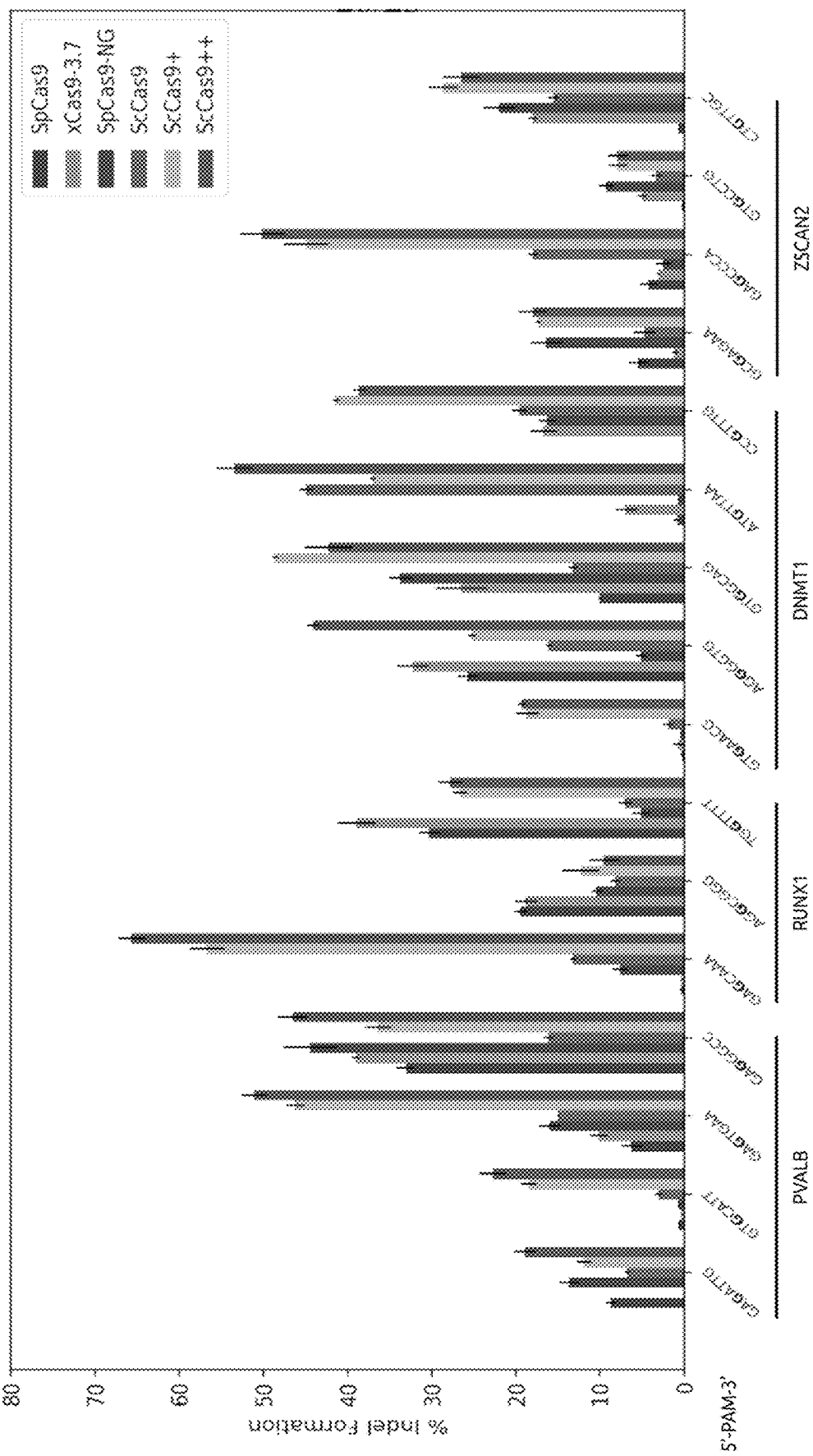

In contrast, Sc+ and Sc++ improve greatly upon the editing capabilities of the wild-type ScCas9 enzyme, demonstrating nearly 3-fold improvement in indel formation efficiency on certain 5'-NNGC-3' targets, and even editing sites at which ScCas9, xCas9-3.7, and SpCas9-NG have negligible activity. FIG. 21 is a graph depicting a quantitative analysis of nucleolytic editing with single G PAM Cas9 variants. Indel frequencies were determined via the TIDE algorithm following PCR amplification of indicated genomic loci, in comparison to unedited controls for each gene target. All samples were performed in duplicates and quantified indel formation values were averaged. Standard deviation was used to calculate error bars.

Figure 22:
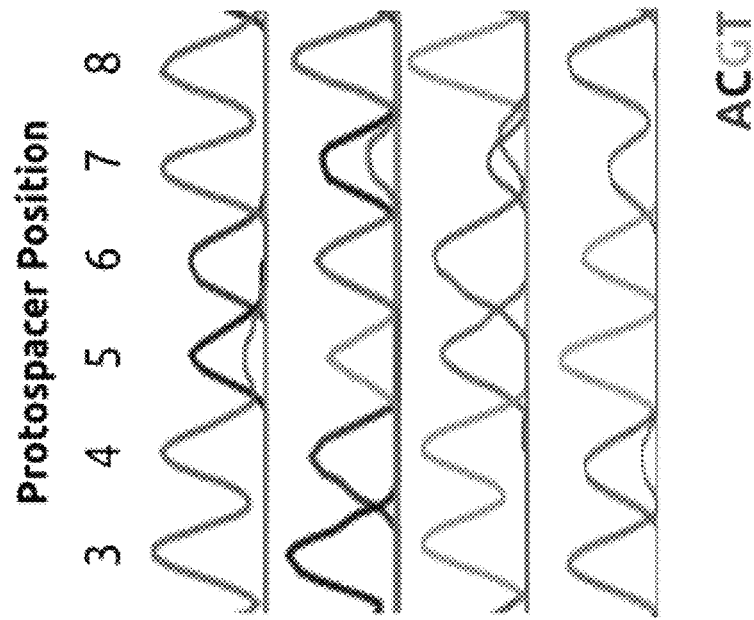

The D10A nickase version of ScCas9+ was subsequently incorporated into the BE3 base editing architecture to examine whether the engineered ScCas9 variants may enable successful C→T base conversion. Following transfection of the ScCas9+BE3 plasmid and plasmids encoding sgRNAs directed at 4 genomic sites with PAM sequences representing each base at both flanking positions (Table 2), evident C→T base editing activities in the 5-nucleotide editing window were observed, in comparison to the unedited control, demonstrating that the engineered variants can be further utilized for base editing purposes. Together, this data suggests that Sc+ and Sc++ are efficient, broad-targeting enzymes that can be harnessed for diverse genome editing applications. FIG. 22 illustrates a quantitative analysis of C→T base editing with ScCas9+BE3. C→T conversion frequencies were determined via the BEEP algorithm, in comparison to unedited controls, following PCR amplification of targeted genomic loci. All samples were performed in duplicates and quantified base editing values were averaged.

Mismatch Tolerance Profile of a High-Fidelity Sc++ Nuclease

Figure 23:
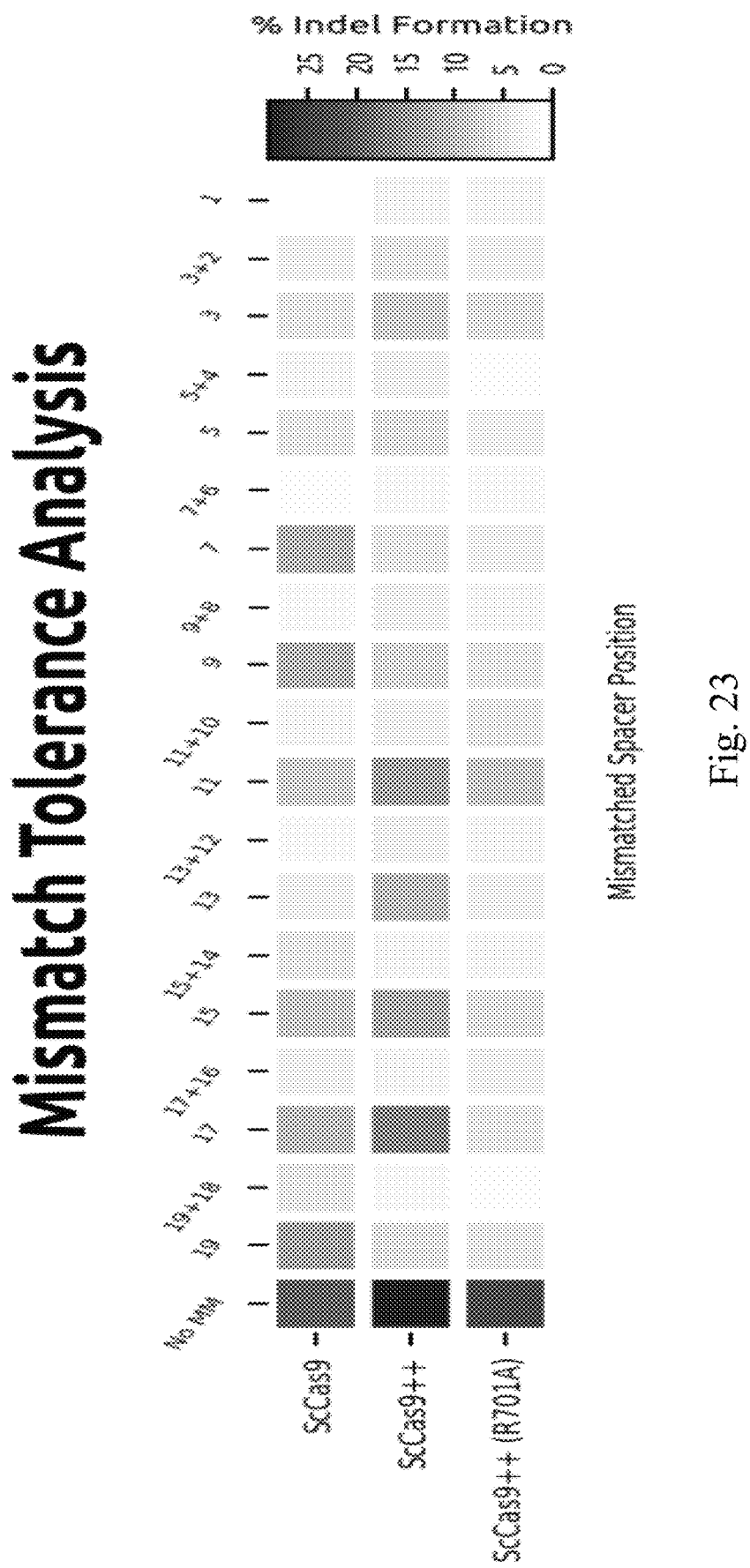

To assess the off-target propensity of the engineered nucleases, a mismatch tolerance assay [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)] was conducted, employing sgRNAs harboring double or single mismatches to a fixed protospacer in the endogenous DNMT1 gene with a non-canonical 5'-CCGT-3' PAM sequence (Table 2). Following TIDE analysis, it was observed that ScCas9 and Sc++ share similar mismatch tolerance profiles across the spacer sequence, as shown in FIG. 23. FIG. 23 is an efficiency heatmap of a mismatch tolerance assay on a genomic target, according to one aspect of the invention, wherein quantified indel frequencies, as assessed by the TIDE algorithm, are exhibited for each labeled single or double mismatch in the sgRNA sequence for the indicated Cas9 variant. The target protospacer sequence within the DNMT1 gene is 5'-GGTCTAGAACCCTCTGGGGA-3' [SEQ ID No: 18], possessing a PAM sequence of 5'-CCGTTTG-3'.

Overall, double mismatches are tolerated less than single mismatches, and mismatches within the PAM-distal region of the spacer generally allow higher editing rates. As Sc++ possesses higher efficiency overall, however, the magnitude of activity for mismatched spacer sequences is greater. Thus, to ameliorate the mismatch tolerance of Sc++, a high-fidelity variant harboring the R701A mutation was engineered, which was previously isolated via high-throughput bacterial selection for SpCas9 to maintain high on-target activity while reducing off-target editing [C. A. Vakulskas, D. P. Dever, G. R. Rettig, R. Turk, A. M. Jacobi, et al., "A high-fidelity Cas9 mutant delivered as a ribonucleoprotein complex enables efficient gene editing in human hematopoietic stem and progenitor cells", Nat. Medicine 24, 1216-1224 (2018)]. The engineered variant demonstrated a slight reduction in on-target editing from that of Sc++, but exhibited reduced activity on mismatched sequences. Overall, these results motivate the usage of this high-fidelity Sc++ for broad and efficient genome editing with reduced mismatch tolerance.

Materials and Methods

Identification of Cas9 Homologs and Generation of Plasmids. The UniProt database [The UniProt Consortium, "UniProt: the universal protein knowledgebase", Nucleic Acids Res. 45, D158-D169 (2017)] was mined for all *Streptococcus* Cas9 protein sequences, which were used as inputs to either the BioPython painvise2 module or Geneious to conduct global pairwise alignments with SpCas9, using the BLOSUM62 scoring matrix [S. Henikoff, J. G. Henikoff, "Amino acid substitution matrices from protein blocks", Proc. Natl. Acad. Sci. 89, 10915-10919 (1992), and subsequently calculate percent homology. The Cas9 from *Streptococcus canis* was codon optimized for *E. Coli*, ordered as multiple gBlocks from Integrated DNA Technologies (IDT), and assembled using Golden Gate Assembly. The pSF-EF1-Alpha-Cas9WT-EMCV-Puro (OG3569) plasmid for human expression of SpCas9 was purchased from Oxford Genetics, and the ORFs of Cas9 variants were individually amplified by PCR to generate 35 bp extensions for subsequent Gibson Assembly into the OG3569 backbone. The pX330-SpCas9-NG (Addgene Plasmid #117919) and xCas9 3.7 (Addgene Plasmid #108379) were gifts from Osamu Nureki and David Liu, respectively. The Cas9 from *S. canis* was codon optimized for human cell expression, ordered as multiple gBlocks from Integrated DNA Technologies (IDT), and assembled using Gibson Assembly into a mammalian expression backbone harboring an EF1α promoter and coexpressing GFP.

Engineering of the coding sequence of ScCas9 to generate the T1227K, *S. anginosus* loop, and R701A substitutions were conducted using the KLD Enzyme Mix (NEB) following PCR amplification with mutagenic primers (Genewiz). Engineering of the coding sequence of ScCas9 and SpCas9 for removal or insertion of motifs was conducted using either the Q5 Site-Directed Mutagenesis Kit (NEB) or Gibson Assembly.

To assemble ScCas9 base editing plasmids, pCMV-ABE (7.10) (Addgene plasmid #102919) and pCMV-BE3 (Addgene plasmid #73021) were received as gifts from David Liu. Similarly, the ORF of the ScCas9 D10A nickase was amplified by PCR to generate 35 bp extensions for subsequent Gibson Assembly into each base editing architecture backbone. sgRNA plasmids were constructed by annealing oligonucleotides coding for crRNA sequences as well as 4 bp overhangs, and subsequently performing a T4 DNA Ligase-mediated ligation reaction into a plasmid backbone immediately down-stream of the human U6 promoter sequence. Assembled constructs were transformed into 50 µL NEB Turbo Competent *E. coli* cells, and plated onto LB agar supplemented with the appropriate antibiotic for subsequent sequence verification of colonies and plasmid purification.

PAM-SCANR Assay. Plasmids for the SpCas9 sgRNA and PAM-SCANR genetic circuit, as well as BW25113 ΔlacI cells, were generously provided by the Beisel Lab (North Carolina State University). Plasmid libraries containing the target sequence followed by either a fully-randomized 8-bp 5'-NNNNNNNN-3' library or fixed PAM sequences were constructed by conducting site-directed mutagenesis, utilizing the KLD enzyme mix (NEB) after plasmid amplification, on the PAM-SCANR plasmid flanking the protospacer sequence (5'—CGAAAGGTTTTGCACTCGAC-3') [SEQ ID No: 5]. Nuclease-deficient mutations (D10A and H850A) were introduced to the ScCas9 variants using Gibson Assembly. The provided BW25113 cells were made electrocompetent using standard glycerol wash and resuspension protocols. The PAM library and sgRNA plasmids, with resistance to kanamycin (Kan) and carbenicillin (Crb) respectively, were co-electroporated into the electrocompetent cells at 2.4 kV, outgrown, and recovered in Kan+Crb Luria Broth (LB) media overnight. The outgrowth was diluted 1:100, grown to ABS600 of 0.6 in Kan+Crb LB liquid media, and made electrocompetent. Indicated dCas9 plasmids, with resistance to chloramphenicol (Chl), were electroporated in duplicates into the electrocompetent cells harboring both the PAM library and sgRNA plasmids, outgrown, and collected in 5 mL Kan+Crb+Chl LB media. Overnight cultures were diluted to an AB S600 of 0.01 and cultured to an OD600 of 0.2. Cultures were analyzed and sorted on a FACSAria machine (Becton Dickinson).

Events were gated based on forward scatter and side scatter and fluorescence was measured in the FITC channel (488 nm laser for excitation, 530/30 filter for detection), with at least 30,000 gated events for data analysis. Sorted GFP-positive cells were grown to sufficient density, and plasmids from the pre-sorted and sorted populations were then isolated, and the region flanking the nucleotide library was PCR amplified and submitted for Sanger sequencing (Genewiz). Bacteria harboring non-library PAM plasmids, performed in duplicates, were analyzed by FACS following electroporation and overnight incubation, and represented as the percent of GFP-positive cells in the population, utilizing standard deviation to calculate error bars. Additional details on the PAM-SCANR assay can be found in Leenay, et al. [R. T. Leenay, K. R. Maksimchuk, R. A. Slotkowski, R. N. Agrawal, A. A. Gomaa, et al., "Identifying and Visualizing Functional PAM Diversity across CRISPR-Cas Systems", Mol. Cell 62, 137-147 (2016].

Figure 24:
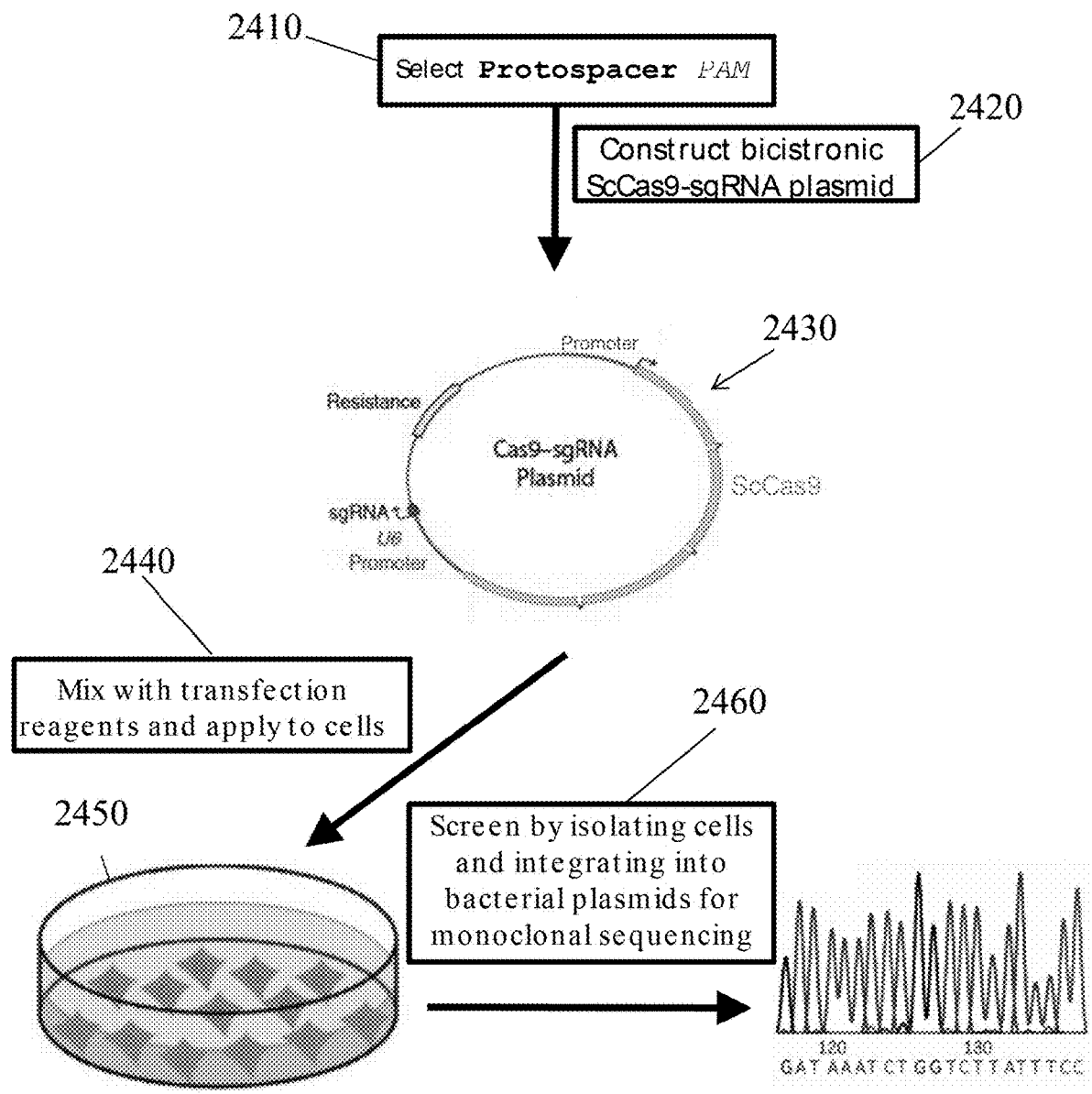
FIG. 24 is a schematic depicting an example workflow to knockout a gene [SEQ ID NO: 43] in cell culture, using ScCas9 according to an aspect of the invention.

Cell Culture and Gene Modification Analysis. FIG. 24 is a schematic depicting an example workflow to knockout a gene in cell culture, using ScCas9 according to an aspect of the invention. As seen in FIG. 24, an example workflow to knockout a gene in cell culture begins with the user's preferred method of selecting 2410 a gRNA target adjacent to an ScCas9-specified PAM around a gene of interest from a FASTA sequence file corresponding to this region. Next, a bicistronic vector containing both the gRNA under the control of a U6 promoter and either the coding sequence of the invention or that of its engineered variants, under the control of a mammalian constitutive promoter, is constructed 2420 using existing assembly and cloning techniques. Subsequently, the plasmid 2430 can be delivered 2440 using a standard lipofection reagent (e.g. TransIT-X2 from Minis Bio LLC) into cell culture. After roughly two days of incubation 2450, individual cells are harvested for genomic extraction to allow an approximately one kilobase (kb) window around the target to be amplified via polymerase chain reaction (PCR). The PCR product is ligated 2460 into a bacterial plasmid with a drug selection marker through blunt end cloning and transformed into *E. coli*. Bacterial colonies are subsequently picked for monoclonal Sanger sequencing and can be carried out by services such as Genewiz.

HEK293T cells were maintained in DMEM supplemented with 100 units/ml penicillin, 100 mg/ml streptomycin, and 10% fetal bovine serum (FBS). For the initial ScCas9+ experiments, sgRNA plasmids (500 ng) and effector (nuclease, BE3, or ABE(7.10)) plasmid (500 ng) were transfected into cells as duplicates ($2 \times 10^5$/well in a 24-well plate) with Lipofectamine 2000 (Invitrogen) in Opti-MEM (Gibco). After 48 hours post-transfection, genomic DNA was extracted using QuickExtract Solution (Epicentre), and genomic loci were amplified by PCR utilizing the KAPA HiFi HotStart ReadyMix (Kapa Biosystems).

For base editing analysis, amplicons were purified and submitted for Sanger sequencing (Genewiz). For indel analysis, the T7E1 reaction was conducted according to the manufacturer's instructions and equal volumes of products were analyzed on a 2% agarose gel stained with SYBR Safe (Thermo Fisher Scientific). Unprocessed gel image files were analyzed in Fiji [J. Schindelin, I. Arganda-Carreras, E. Frise, V. Kaynig, M. Longair, et al., "Fiji: an open-source platform for biological-image analysis. Nat. Methods 9, 676-682 (2012)]. The cleaved bands of interest were isolated using the rectangle tool, and the areas under the corresponding peaks were measured and calculated as the fraction cleaved of the total product. Percent gene modification was calculated as follows [D. Y. Guschin, A. J. Waite, G. E. Katibah, J. C. Miller, M. C. Holmes, et al., "A Rapid and General Assay for Monitoring Endogenous Gene Modification", Methods Mol. Biol. 649, 247-256 (2010]:

$$\% \text{ gene modification} = 100 \times (1 - (1-\text{fraction cleaved})^{1/2})$$

All samples were performed in duplicates and percent gene modifications were averaged. Standard deviation was used to calculate error bars.

For follow-on and ScCas9++ experiments, sgRNA plasmids (100 ng) and effector (nuclease and BE3) plasmids (100 ng) were transfected into cells as duplicates ($2 \times 10^4$/well in a 96-well plate) with Lipofectamine 3000 (Invitrogen) in Opti-MEM (Gibco). After 5 days post-transfection, genomic DNA was extracted using QuickExtract Solution (Epicentre), and genomic loci were amplified by PCR utilizing the Phusion Hot Start Flex DNA Polymerase (NEB). Amplicons were enzymatically purified and submitted for Sanger sequencing (Genewiz). Sanger sequencing ab1 files were either analyzed using the TIDE algorithm (tide.deskgen.com) in comparison to an unedited control to calculate indel frequencies, or by the internally-developed BEEP software for base editing analysis. All samples were performed in duplicates and modification values were averaged. Standard deviation was used to calculate error bars.

Base editing analysis with Traffic Light Reporter. HEK293T cells were maintained as previously described, and transfected with the corresponding sgRNA plasmids (333 ng), ABE7.10 plasmids (333 ng), and synthetically constructed TLR plasmids (333 ng) into cells as duplicates (2×105/well in a 24-well plate) with Lipofectamine 2000 (Invitrogen) in Opti-MEM (Gibco). After 5 days post-transfection, cells were harvested and analyzed on a FACS-Celesta machine (Becton Dickinson) for mCherry (561 nm laser excitation, 610/20 filter for detection) and GFP (488 nm laser excitation, 530/30 filter for detection) fluorescence. Cells expressing mCherry were gated and percent GFP calculation of the subset were calculated. All samples were performed in duplicates and percentage values were averaged. Standard deviation was used to calculate error bars. The TLR spacer sequence is 5'-TTCTGTAGTCGACGGTACCG-3' [SEQ ID No: 6].

Base Editing Evaluation Program. The Base Editing Evaluation Program (BEEP) was written in Python, employing the pandas data manipulation library and BioPython package. As inputs, the program requires a sample ab1 file, a negative control ab1 file, a target sequence, as well as the position of the specified base conversion, either handled as a .csv file for multiple sample analysis or for individual samples on the command line. Briefly, the provided target sequences are aligned to the base-calls of each input ab1 file to determine the absolute position of the target within the file. Subsequently, the peak values for each base at the indicated position in the spacer are obtained, and the editing percentage of the specified base conversion is calculated. Finally, a separate function normalizes the editing percentage to that of the negative control ab1 file to account for background signals of each base. The final base conversion percentage is outputted to the same .csv file for downstream analysis.

SPAMALOT Pipeline. All 11,440 *Streptococcus* bacterial and 53 *Streptococcus* associated phage genomes were downloaded from NCBI. CRISPR repeats catalogued for the genus were downloaded from CRISPRdb hosted by University of Paris-Sud [I. Grissa, G. Vergnaud, C. Pourcel, "The CRISPRdb database and tools to display CRISPRs and to generate dictionaries of spacers and repeats", BMC Bioinform. 8, 172 (2007)]. For each genome, spacers upstream of a specific repeat sequence were collected with a toolchain consisting of the fast and memory-efficient Bowtie 2 alignment [B. Langmead, S. L. Salzberg, "Fast gapped-read alignment with Bowtie 2", Nat. Methods 9, 357359 (2012)]. Each genome and repeat-type specific collection of spacers were then matched to all phage genomes using the original Bowtie short-sequence alignment tool [B. Langmead, C. Trapnell, M. Pop, S. L. Salzberg, "Ultrafast and memory-efficient alignment of short DNA sequences to the human genome", Genome Biol. 10, R25 (2009)] to identify candidate protospacers with at most one, two, or no mismatches. Unique candidates were input into the WebLogo 3 [Crooks, G. E. et al. "WebLogo: a sequence logo generator", Genome Res. 14, 1188-1190 (2004)] command line tool for prediction of PAM features.

Statistical analysis. Data are shown as mean±s.d., unless stated otherwise. Statistical analysis was performed using the two-tailed Students t-test, utilizing the SciPy software package. Calculated p-values, as compared to the negative control, are represented as follows: *P≤0.05, P≤0.01, *P≤0.001, and ****P≤0.0001. Data was plotted using Matplotlib.

The present invention demonstrates the natural PAM plasticity of a highly similar, yet previously uncharacterized, Cas9 from *Streptococcus canis* (ScCas9) through rational manipulation of distinguishing motif insertions. Affinity to minimal 5'-NNG-3' PAM sequences and the accurate editing capabilities of the ortholog in both bacterial and human cells have been demonstrated. In one aspect of the invention, an automated bioinformatics pipeline, the Search for PAMs by ALignment Of Targets (SPAMALOT) further explores the microbial PAM diversity of otherwise-overlooked *Streptococcus* Cas9 orthologs. The results establish that ScCas9 can be utilized both as an alternative genome editing tool and as a functional platform to discover novel *Streptococcus* PAM specificities.

At least the following aspects, implementations, modifications, and applications of the described technology are contemplated by the inventors and are considered to be aspects of the presently claimed invention:

(1) An isolated, engineered *Streptococcus canis* Cas9 (ScCas9) protein with its PID being the PID amino acid composition of SpCas9-NG.

(2) An isolated, engineered ScCas9 protein having a threonine-to-lysine substitution mutation at position 1227 in its amino acid sequence.

(3) An isolated, engineered ScCas9 protein having a threonine-to-lysine substitution mutation at position 1227 in its amino acid sequence and a substitution of residues ADKKLRKRSGKLATE [SEQ ID No: 4] in position 365-379 in the ScCas9 open reading frame, in addition to the T1227K substitution (Sc++).

(4) CRISPR-associated DNA endonucleases with a PAM specificity of 5'-NG-3' or 5'-NNG-3'.

(5) A method of altering expression of at least one gene product, comprising steps of introducing, into a eukaryotic cell containing and expressing a DNA molecule having a target sequence and encoding the gene product, an engineered, non-naturally occurring Clustered Regularly Interspaced Short Palindromic Repeats (CRISPR)—CRISPR-associated (Cas) (CRISPR-Cas) system comprising one or more vectors comprising:
  (a) a regulatory element operable in a eukaryotic cell operably linked to at least one nucleotide sequence encoding a CRISPR system guide RNA that hybridizes with the target sequence, and
  (b) a second regulatory element operable in a eukaryotic cell operably linked to a nucleotide sequence encoding at least one protein selected from the group comprising an isolated, engineered *Streptococcus canis* Cas9 (ScCas9) protein with its PID as the PID amino acid composition of SpCas9-NG and an isolated, engineered ScCas9 protein with its harboring a threonine-to-lysine substitution mutation at position 1227 in its amino acid sequence, wherein components (a) and (b) are located on same or different vectors of the system, whereby the guide RNA targets the target sequence and one or more of the proteins cleave the DNA molecule, whereby expression of the at least one gene product is altered and wherein the proteins and the guide RNA do not naturally occur together.

While preferred embodiments of the invention are disclosed herein, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. An isolated, engineered Clustered Regularly Interspaced Short Palindromic Repeats (CRISPR)-associated *Streptococcus canis* Cas9 (ScCas9) DNA endonuclease, modified with a Protospacer Adjacent Motif (PAM) interacting domain (PID) of *Streptococcus pyogenes* Cas9 (SpCas9)-NG, which replaces the ScCas9 PID, and further comprising a 2-amino acid insertion of "KQ" one amino acid position N-terminus of the first critical arginine (R) residue for PAM binding.

2. The ScCas9 DNA endonuclease of claim 1, further comprising the substitution of amino acids 365-379 in ScCas9 (SEQ ID NO: 27) with amino acids ADKKLRKRSGKLATE (SEQ ID No: 4).

3. The ScCas9 DNA endonuclease of claim 2, wherein said ScCas9 (SEQ ID NO: 27) is further modified with a threonine-to-lysine substitution at position 1227.

4. The ScCas9 DNA endonuclease of claim 1, wherein said ScCas9 (SEQ ID NO: 27) is further modified with a threonine-to-lysine substitution at position 1227.

5. A method for altering expression of at least one gene product comprising employing an engineered *Streptococcus canis* Cas9 (ScCas9) endonuclease in complex with guide RNA, wherein the ScCas9 endonuclease is modified with a Protospacer Adjacent Motif (PAM) interacting domain (PID) of *Streptococcus pyogenes* Cas9 (SpCas9)-NG, which replaces the ScCas9 PID, and further modified with a 2-amino acid insertion of "KQ" one amino acid position N-terminus of the first critical arginine (R) residue for PAM binding, having specific recognition and activity on a DNA target immediately upstream of either an "NG" or "NNG" PAM sequence.

6. The method of claim 5, wherein said engineered ScCas9 DNA endonuclease further comprises:
(i) the substitution of amino acid positions 365-379 of SEQ ID NO: 27 with amino acids (SEQ ID NO: 4)
ADKKLRKRSGKLATE, and/or
(ii) a threonine-to-lysine substitution at position 1227 of SEQ ID No: 27.

7. A method of altering expression of at least one gene product, comprising:
introducing, into a eukaryotic cell containing and expressing a DNA molecule having a target sequence and encoding the gene product, an engineered, non-naturally occurring Clustered Regularly Interspaced Short Palindromic Repeats (CRISPR)-CRISPR-associated (Cas) (CRISPR-Cas) system comprising one or more vectors comprising:
(a) a first regulatory element, operable in a eukaryotic cell, operably linked to at least one nucleotide sequence encoding a CRISPR system guide RNA that hybridizes with the target sequence; and
(b) a second regulatory element, operable in a eukaryotic cell, operably linked to a nucleotide sequence encoding an engineered *Streptococcus canis* Cas9 (ScCas9) DNA endonuclease, wherein said engineered ScCas9 DNA endonuclease is modified with a Protospacer Adjacent Motif (PAM) interacting domain (PID) of *Streptococcus pyogenes* Cas9 (SpCas9)-NG, which replaces the ScCas9 PID, and further modified with a 2-amino acid insertion of "KQ" one amino acid position N-terminus of the first critical arginine (R) residue for PAM binding, and has a Protospacer Adjacent Motif (PAM) specificity of 5'-NG-3' or 5'-NNG-3' and wherein components (a) and (b) are located on the same or different vectors of the system, whereby the guide RNA targets the target sequence and one or more of the endonucleases cleave the DNA molecule, whereby expression of the at least one gene product is altered, and wherein the DNA endonucleases and the guide RNA do not naturally occur together.

8. The method of claim 7, wherein said engineered ScCas9 DNA endonuclease further comprises:
   (i) the substitution of amino acid positions 365-379 of SEQ ID NO: 27 with amino acids ADKKLRKRSGKLATE (SEQ ID No: 4),

```
                                          (SEQ ID NO: 4)
   ADKKLRKRSGKLATE,
``` and/or
   (ii) a threonine-to-lysine substitution at position 1227 of SEQ ID No: 27.

\* \* \* \* \*